(12) United States Patent
Green et al.

(10) Patent No.: US 11,547,997 B2
(45) Date of Patent: Jan. 10, 2023

(54) INTEGRATED DIAGNOSTIC DEVICES HAVING EMBEDDED BIOMOLECULAR COMPUTING SYSTEMS AND USES THEREOF

(71) Applicant: Arizona Board of Regents on behalf of Arizona State University, Scottsdale, AZ (US)

(72) Inventors: Alexander A. Green, Scottsdale, AZ (US); Matthew Gilliam, Tempe, AZ (US); Kirstie Swingle, Phoenix, AZ (US); Nicholas Stephanopoulos, Scottsdale, AZ (US); Neal Woodbury, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 34 days.

(21) Appl. No.: 16/603,338

(22) PCT Filed: Apr. 6, 2018

(86) PCT No.: PCT/US2018/026455
§ 371 (c)(1),
(2) Date: Oct. 7, 2019

(87) PCT Pub. No.: WO2018/187687
PCT Pub. Date: Oct. 11, 2018

(65) Prior Publication Data
US 2020/0386750 A1    Dec. 10, 2020

Related U.S. Application Data

(60) Provisional application No. 62/483,110, filed on Apr. 7, 2017.

(51) Int. Cl.
| | | |
|---|---|---|
| *B01L 3/00* | (2006.01) | |
| *C12Q 1/70* | (2006.01) | |
| *G01N 33/543* | (2006.01) | |

(52) U.S. Cl.
CPC ........ *B01L 3/502715* (2013.01); *C12Q 1/702* (2013.01); *G01N 33/54366* (2013.01);
(Continued)

(58) Field of Classification Search
None
See application file for complete search history.

(56) References Cited

U.S. PATENT DOCUMENTS 4,144,306 A * 3/1979 Figueras .................. C12Q 1/40
                                                    422/423
4,337,065 A * 6/1982 Hiratsuka ........ G01N 33/54386
                                                    422/423
(Continued)

FOREIGN PATENT DOCUMENTS

WO    2015061480 A1    4/2015
WO    2016028497 A1    2/2016
(Continued)

OTHER PUBLICATIONS

Carlson, R.. The Changing Economics of DNA Synthesis. Nat. Biotechnol 2009. vol. 27, 12, 1091-1094.
(Continued)

*Primary Examiner* — Melanie Brown
(74) *Attorney, Agent, or Firm* — Quarles & Brady, LLP

(57) ABSTRACT

Integrated diagnostic devices comprising peptide-DNA conjugates for analyte detection, an embedded biomolecular computing system for sample analysis, and a layered device architecture are provided herein. In particular, provided herein are devices comprising a layered architecture that enables diagnostic reagents, sample components, and reac-
(Continued)

tion products to flow through the system with minimal user intervention.

10 Claims, 14 Drawing Sheets

Specification includes a Sequence Listing.

(52) U.S. Cl.
CPC ............... *G01N 33/54386* (2013.01); *B01L 2300/0627* (2013.01); *G01N 2458/10* (2013.01)

(56) References Cited

U.S. PATENT DOCUMENTS

| 4,472,498 | A | * | 9/1984 | Masuda | G01N 33/521 422/421 |
|---|---|---|---|---|---|
| 2005/0170362 | A1 | * | 8/2005 | Wada | G01N 33/538 435/6.13 |
| 2006/0199236 | A1 | * | 9/2006 | Talebpour | G01N 33/536 435/7.92 |
| 2009/0110601 | A1 | * | 4/2009 | Levi | G01N 33/54386 422/68.1 |
| 2009/0305253 | A1 | * | 12/2009 | Breaker | G01N 33/542 435/6.11 |
| 2012/0003630 | A1 | | 1/2012 | Collins | |
| 2014/0246334 | A1 | | 9/2014 | Bosch et al. | |
| 2015/0017639 | A1 | | 1/2015 | Wong, Jr. et al. | |
| 2019/0071737 | A1 | | 3/2019 | Green | |
| 2019/0185856 | A1 | | 6/2019 | Green | |
| 2019/0218624 | A1 | | 7/2019 | Green | |
| 2019/0256898 | A1 | | 8/2019 | Green | |
| 2019/0276901 | A1 | | 9/2019 | Green | |
| 2019/0285620 | A1 | | 9/2019 | Green | |

FOREIGN PATENT DOCUMENTS

| WO | 2017040829 | A1 | 3/2017 |
| WO | 2017147585 | A1 | 8/2017 |
| WO | 2017205668 | A1 | 11/2017 |
| WO | 2018026762 | A1 | 2/2018 |
| WO | 2018026765 | A1 | 2/2018 |
| WO | 2018027177 | A1 | 2/2018 |
| WO | 2018075502 | A1 | 4/2018 |
| WO | 2018093898 | A1 | 5/2018 |
| WO | 2018112350 | A1 | 6/2018 |

OTHER PUBLICATIONS

Cheng, H., et al. "Recent development of transient electronics." Theoretical and Applied Mechanics Letters 6.1 (2016): 21-31.
Das, J., et al. "An ultrasensitive universal detector based on neutralizer displacement." Nature chemistry 4.8 (2012): 642.
Engelen, W., et al. Antibody-Controlled Actuation of DNA-based Molecular Circuits. Nat. Commun. 2017. 8 14473.
Frascione, N., et al. "Fluorogenic displacement biosensors for PSA detection using antibody-functionalised quantum dot nanoparticles." RSC Advances 5.9 (2015): 6595-6598.
Green, A. A., et al. Toehold Switches: De-Novo-Designed Regulators of Gene Expression. Cell 2014. 159, 925-939. http://dx.doi.org/10.1016/j.cell.2014.10.002.
Green, A. A., et al. "Complex cellular logic computation using ribocomputing devices." Nature 548.7665 (2017): 117.
Han, K. et al. "Design strategies for aptamer-based biosensors." Sensors 10.5 (2010): 4541-4557.
Holstein, C. A., et al. Immobilizing affinity proteins to nitrocellulose: a toolbox for paper-based assay developers. Anal Bioanal Chem. 2015. DOI 10.1007/S00216-015-9052-0.
Hwang, S.-W., et al. "A physically transient form of silicon electronics." Science 337.6102 (2012): 1640-1644.
International Searching Authority, International Search Report and Written Opinion for application PCT/US2018/026455, dated Jun. 27, 2018.
Keefe, A. D., et al. One-Step Purification of Recombinant Proteins Using a Nanomolar-Affinity Streptavidin-Binding Peptide, the SBP-Tag. Protein Expression and Purification. 2001. 23, 440-446. doi:10.1006/prep.2001.1515.
Lutz, B. et al. "Dissolvable fluidic time delays for programming multistep assays in instrument-free paper diagnostics" Lab Chip 2013, 13, 2840.
Pardee, K., et al. Paper-Based Synthetic Gene Networks. Cell 2014. 159, 940-954. http://dx.doi.org/10.1016/j.cell.2014.10.004.
Pardee, K., et al. Rapid, Low-Cost Detection of Zika Virus Using Programmable Biomolecular Components. Cell 2016. 165, 1255-1266. http://dx.doi.org/10.1016/j.cell.2016.04.059.
Purexpress In Vitro Protein Synthesis instruction manual. New England BioLabs, 2009.
Sherman, W. B. et al. A precisely controlled DNA biped walking device. Nano Lett. 2004. 4, 1203-1207.
Shin, J. S. et al. A synthetic DNA walker for molecular transport. J. Am. Chem. Soc. 2004. 126, 10834-10835.
U.S. Appl. No. 16/303,937.
U.S. Appl. No. 16/322,719.
U.S. Appl. No. 16/349,752.
Windergren, J., et al. Fluorescence Correlation Spectroscopy of Triplet States in Solution: A theoretical and Experimental Study. J. Phys. Chem. 1995. 99, 13368-13379.
Yan, H., et al. A robust DNA mechanical device controlled by hybridization topology. Nature. 2002. 415, 62-65.
Yurke, B., et al. L. A DNA fueled molecular machine made of DNA. Nature 2000. 406, 605-608.
Zhang, D. Y., et al. Dynamic DNA Nanotechnology using Strand displacement reactions. Nat. Chem.. 2011.3, 103-113.
Zhong, H. et al. RNA used to control a DNA rotary nanomachine. Nano Lett. 2006. 6, 2899-2903.

* cited by examiner

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: PSA peptide

<400> SEQUENCE: 1

Asp Val Cys Ala Gln Val
1               5

<210> SEQ ID NO 2
<211> LENGTH: 38
<212> TYPE: PRT
<213> ORGANISM: Artificial Sequence
<220> FEATURE:
<223> OTHER INFORMATION: Streptavidin Binding Peptide

<400> SEQUENCE: 2

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 3
<211> LENGTH: 36
<212> TYPE: DNA
<213> ORGANISM: Artificial Sequence
<220> FEATURE:
<223> OTHER INFORMATION: FER1_T16 DNA trigger sequence

<400> SEQUENCE: 3
gcagaaacta acagaagcca aatcaattac atacta                         36

<210> SEQ ID NO 4
<211> LENGTH: 7
<212> TYPE: PRT
<213> ORGANISM: Artificial Sequence
<220> FEATURE:
<223> OTHER INFORMATION: alpha tubulin peptide DM1A

<400> SEQUENCE: 4

Ala Ala Leu Glu Lys Asp Tyr
1               5
```

INTEGRATED DIAGNOSTIC DEVICES HAVING EMBEDDED BIOMOLECULAR COMPUTING SYSTEMS AND USES THEREOF

CROSS-REFERENCE TO RELATED APPLICATIONS

This application represents the national stage entry of PCT International Application No. PCT/US2018/026455, filed on Apr. 6, 2018, and claims the benefit of U.S. Provisional Application Ser. No. 62/483,110, filed on Apr. 7, 2017, which is incorporated by reference herein as if set forth in its entirety.

STATEMENT REGARDING FEDERALLY SPONSORED RESEARCH

N/A

BACKGROUND

The emergence of the deadly Ebola virus and the rapid spread of the Zika virus have revealed critical gaps in the ability of healthcare systems worldwide to respond to infectious diseases. Current diagnostic technologies for infectious diseases identify pathogens by detecting the nucleic acids or antibody proteins produced by the immune system in response to infection, but both have drawbacks. For example, previously described tests that combine isothermal nucleic acid amplification reactions with paper-based cell-free reactions and toehold switches for virus detection are substantially cheaper, faster, and easier to implement than commercially available nucleic acid assays, but still require equipment for regulating reaction temperature, pipettes to transfer liquids between assay steps, and several hours to wait for results. As such, the test remains confined to clinics with basic equipment, electricity, and a skilled technician. Moreover, the test is limited to detecting nucleic acids, which precludes its application to detecting other biomarkers such as proteins and antibodies. Accordingly, there remains a need in the art for improved diagnostic devices for detecting pathogens and disease states.

SUMMARY

In one aspect, provided herein is a diagnostic device for detecting a target analyte in a sample. The device can comprise, consist essentially of, or consist of a sample receiving layer, an analyte detection layer, a microfluidic layer, and one or more biomolecular computing layers, wherein the device is configured for transverse liquid flow between the layers. The device can further comprise a nucleic acid amplification layer. At least one of the one or more biomolecular computing layers can be an output layer. The output layer can comprise a nucleic acid-based sensor reaction panel. The nucleic acid-based sensor reaction panel can comprise a plurality of nucleic acid-based sensors. The plurality can comprise nucleic acid-based sensors selected from the group consisting of a riboregulator and an aptasensor. The analyte detection layer can comprise a plurality of peptide-DNA conjugates bound to an antibody or epitope having specificity for the target analyte, wherein binding of the target analyte to the antibody or epitope displaces the peptide-DNA conjugate. The target analyte can be a protein, carbohydrate, or lipid. The layers in the diagnostic device can be separated by one or more transient layers that dissolve in a prescribed amount of time when contacted to a sample to control transverse flow of amplification products, nucleic acids, and sample components through the device. The one or more transient layers can comprise a dried sucrose solution. The microfluidic layer can be configured for lateral flow of amplification products and nucleic acids across the device. The sample receiving layer can comprise a separation membrane. The sample can be a biological sample. The biological sample can be a blood, serum, plasma, urine, or saliva sample. The device can be paper-based.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

Figure 1A:
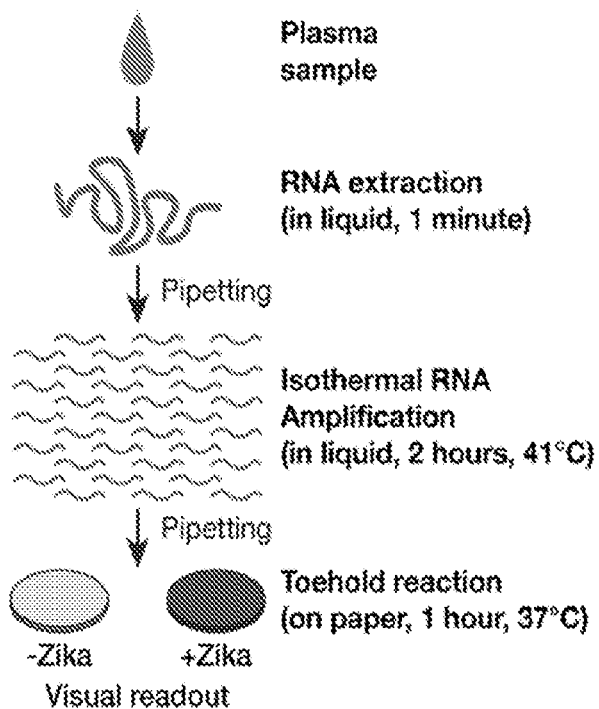
FIGS. 1A-1B illustrate an existing diagnostic system and an exemplary embodiment of the integrated diagnostic devices having biomolecular computing capacity described herein. (A) The recently reported Zika diagnostic device and system employs a brief boiling step to extract RNA from the virus, then an isothermal RNA amplification step in liquid over 2 hours at 41° C., and finally a toehold switch cell-free reaction on paper over 1 hour at 37° C. to provide a visual readout of the test result. Pipetting steps are used to transfer the sample between different stages of the reaction. (B) The proposed integrated diagnostic featuring a layered device architecture and transverse sample flow. A whole blood sample, which can be boiled to extract RNA from virus particles present, is initially separated into plasma using a plasma separation membrane. Protein analytes are detected in a protein detection layer followed by a DNA/RNA amplification layer that amplifies nucleic acids in the original sample and peptide-DNA conjugates from the protein detection layer. Next a microfluidic layer routes the amplified, low-molecular-weight products laterally across the device. In subsequent layers, biomolecular computing layers process the nucleic acid inputs and test results from a panel of different tests are displayed in the final output layer. Liquid is transported through the device using capillary forces.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE DISCLOSURE

All publications, including but not limited to patents and patent applications, cited in this specification are herein incorporated by reference as though set forth in their entirety in the present application.

Simple, low-cost, and rapid diagnostic devices like home pregnancy tests and blood glucose meters have transformed healthcare over the past four decades, enabling people to monitor and take charge of their health in non-clinical settings. Developing simple, low-cost, and rapid devices that integrate nucleic acid and protein detection with biomolecular computing in a single device for pathogen identification would enable a large range of viruses, microbes, and genetic diseases to be identified in the same test.

Accordingly, embodiments described herein relate to integrated diagnostic devices and systems that combine nucleic acid signals derived from protein and nucleic acid detection events with biomolecular computing to analyze a sample and provide test results without outside intervention or additional information processing. Embodiments described herein also relate to methods for construction of such integrated diagnostic devices and as well as testing systems for analyte (e.g., pathogen antigen) detection and identification using liquid biological samples such as serum, plasma, blood, saliva, and urine. Advantages of the diagnostic devices provided herein include lower cost and lower complexity. For example, devices provided herein require fewer handling steps, which can be a source of error. As the diagnostic devices and systems provided herein operate with minimal human intervention and require almost no laboratory equipment, they can be deployed in a variety of low-instrumentation settings such as homes and non-hospital clinics for fast, specific detection and identification of disease states.

Figure 1B:
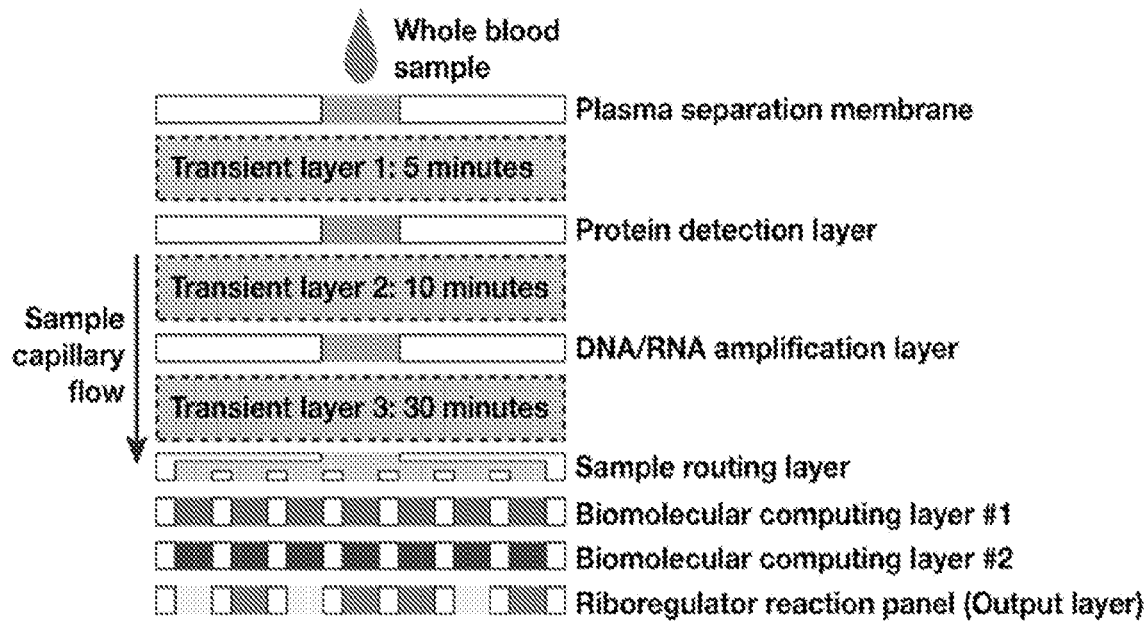

The diagnostic devices and systems provided herein employ an innovative diagnostic platform that employs peptide-DNA conjugates for protein, carbohydrate, or lipid detection; an embedded, autonomous biomolecular computing system; and a layered device architecture that enables the diagnostic reaction to flow through the system without external user intervention. As shown in FIG. 1B, these features and functionalities are hosted in a new layered device architecture in which timed chemical reactions are used to control when and where the required diagnostic reactions occur. This capability eliminates the handling steps typically required after the sample has been applied to the device. These features enable detection of virtually any pathogen or disease state using a single diagnostic device. Furthermore, the diagnostic devices and systems described herein can be deployed in inexpensive paper-based formats, exhibit long-term stability at room temperature, and operate with minimal equipment so that they can be used in the field or the home in low-through high-income countries.

In one aspect, provided herein is a diagnostic device detecting a target analyte in a sample. The diagnostic device can comprise comprising a sample receiving layer, an analyte detection layer, a microfluidic layer, and one or more biomolecular computing layers, wherein the device is configured for transverse liquid flow between the layers. In some cases, the device further comprises a nucleic acid amplification layer. For example, it can be advantageous to include a nucleic amplification layer if the sample does not contain a large concentration of the analyte of interest. As used herein, the terms "analyte" and "target analyte" refer to the molecule or atom to be detected in a test sample. Examples of target analytes include, but are not limited to, a protein, peptide, polypeptide, amino acid, antibody, nucleic acid, oligonucleotide, DNA, RNA, carbohydrate, lipid, hormone, steroid, toxin, vitamin, any drug administered for therapeutic and illicit purposes, a bacterium, a virus, cell, as well as any antigenic substances, haptens, antibodies, metabolites, and combinations thereof.

In some cases, at least one of the one or more biomolecular computing layers is an output layer comprising a nucleic acid-based sensor reaction panel. Preferably, the nucleic acid-based sensor reaction panel comprises a plurality of nucleic acid-based sensors selected from riboregulators (e.g., toehold switch riboregulators), aptamer-based sensors or "aptasensors", and ultraspecific riboregulators. As used herein, the terms "aptamer-based sensor," "aptasensor," and "aptamer beacon" are used interchangeably to refer to a sensor (e.g., biomolecule sensor) that can be used to capture a target analyte by exploiting the affinity of an aptamer to its target. As used herein, the term "ultraspecific riboregulator" refers to a regulator of gene expression, configured to repress or activate translation of an open reading frame, and thus repress or activate production of a protein, only upon recognition of a target RNA with the exact sequence with single nucleotide specificity.

As described herein, the analyte detection layer can comprise a plurality of peptide-DNA conjugates bound to an antibody or epitope having specificity for the target analyte, where binding of the target analyte to the antibody or epitope displaces the peptide-DNA conjugate. For pathogen or disease detection, an exemplary diagnostic embodiment comprises detection of a target protein via release of a peptide-DNA conjugate, the release of which acts as a nucleic acid signal that flows to a biomolecular computing system embedded in the diagnostic device for analysis. Biomolecular computing systems integrate nucleic acid signals derived from protein and nucleic acid detection events to analyze the sample and provide test results without outside intervention or additional information processing. In some cases, results of analysis by the biomolecular computing system are detected as colorimetric results produced through an enzymatic reaction. Preferably, an input protein is obtained from a biological sample of a subject (e.g., human patient). Biological samples appropriate for use according to the methods provided herein include, without limitation, blood, serum, urine, saliva, tissues, cells, and organs. More preferably, the biological sample is a liquid biological sample such as blood, serum, plasma, urine, or saliva obtained from the subject.

As shown in FIG. 1B, an integrated device of the present invention preferably has a layered architecture that sequesters diagnostic reactions to different regions of the device. Preferably, the layered architecture is configured to permit transverse liquid flow through the device without external user intervention after the sample (e.g., a liquid-containing biological sample) has been applied to the device (FIG. 1B). Thus, as the test proceeds, the sample will flow transversely through different layers and undergo the required processing steps. Assay steps such as the isolation of plasma from whole blood, isothermal amplification, and the final RNA detection reaction are each carried out in separate paper layers in the device.

As used herein, the term "transverse" refers to liquid flow that is predominantly perpendicular to the length and width of a layer, and is predominantly in a direction parallel to the depth of a layer. Conversely, lateral flow is predominantly parallel to the length or width planes of a layer. As illustrated in FIG. 1B, transverse flow permits flow of a liquid sample perpendicular to the length and width of each layer such that the sample is drawn from a sample receiving layer to one or more subsequent layers. As will be appreciated by those of skill in the art, the type of liquid flow contemplated in a particular device, assay, or method can vary according to the structure of the device.

In some cases, a whole blood sample, which can be boiled to extract RNA from virus particles present, is initially separated into plasma using a plasma separation membrane. Protein analytes are detected in a protein detection layer followed by a DNA/RNA amplification layer that amplifies nucleic acids in the original sample and peptide-DNA conjugates from the protein detection layer. Next, a microfluidic layer routes the amplified, low-molecular-weight products laterally across the device. In subsequent layers, biomolecular computing layers process the nucleic acid inputs and test results from a panel of different tests are displayed in the final output layer. Liquid is transported through the device using capillary forces.

In certain embodiments, it will be advantageous to provide in a device different processing zones that are spatially and temporally separated. An aqueous sample can pass through such processing zones and encounter one or more dried solutions which provide a timed dissolvable barrier on paper-based devices. Device complexity can be reduced, and device sensitivity increased, through the use of transient layers between active layers of the device. In some embodiments, layers in the diagnostic device are separated by transient layers that dissolve in a predetermined amount of time to control transverse flow of amplification products, nucleic acids, and sample components through the device. In this manner, the transient layer is a fluid flow barrier that acts as a delay mechanism. Using transient layers, it is possible to impede sample flow so that sufficient time is allotted for different diagnostic chemical reactions. For instance, a layer that degrades over 30 minutes to two hours can be used after a layer involved with amplifying nucleic acids to ensure there is sufficient time to make enough nucleic acid copies (FIG. 1B). Accordingly, the addition of one or more fluid flow barriers results in a diagnostic device exhibiting improved sensitivity.

Preferably, transient layers comprise water soluble polymers that are designed to dissolve in a time-dependent manner as they encounter a propagating water front from the sample. In certain embodiments, a transient layer comprises a dried sucrose solution. Sucrose is low cost, highly soluble in water, and has been shown to be useful as a soluble delay material in multistep paper-based lateral flow tests. See Lutz et al. (Lab Chip 2013, 13:2840). Fluid flow through a multi-layer device can be delayed with the addition of a sucrose-treated middle layer. In particular, by varying the concentration of sucrose solution, the amount of time required for fluid to reach the bottom layer can be increased (thus, flow is delayed) by the presence of a 5%-60% or greater sucrose solution (e.g., a 5%, 10%, 15%, 20%, 25%, 30%, 35%, 40%, 45%, 50%, 55%, 66% or greater sucrose solution). As described in Example 1, liquid passaged was delayed by 6±1 minutes using a 20% sucrose solution. Liquid passage can be delayed by 12±3 minutes using a 30% sucrose solution. In some cases, additional delay layers are added between the top and bottom layers in order to provide further control over sample passage.

In some embodiments, the output of the detection layer in the final device is a color change produced from the enzyme beta-galactosidase interacting with a substrate. When the device comprises one or more transient layers comprising a sucrose solution, the sample solution will become more concentrated with sucrose, or more generally the barrier compound, as it dissolves each barrier layer. Since the increased concentration of sucrose can affect the interaction between the enzyme and substrate and in turn the final readout of the device, it is important to test the viability of the enzyme-substrate interaction on paper in the presence of a concentrated sucrose solution. Such a test is described in the Examples that follow.

In some cases, the water soluble polymer of the transient layer is a biocompatible polymer such as, for example, as methyl cellulose, pullulan, poly(vinyl alcohol), polyvinylpyrrolidone, polylacticcoglycolic acid, hydroxypropylmethylcellulose. For example, fluid passage can be delayed by adding thin films of methyl cellulose or pullulan between top and bottom paper-based microfluidic layers. Degradable films comprising water soluble polymers have been widely used in the field of transient electronics for electronic devices that decompose over prescribed (e.g., predetermined) times when implanted in the body (Hwang et al., Science 337, 1640 (2012)). Theory has been developed to model their dissolution times as a function of layer density, thickness, and water diffusivity (Cheng et al., *Theor. Appl. Mech. Lett.* 6, 21 (2016)).

When selecting water soluble material for transient layers, it is important to consider that, when the target analyte for the detection layer is an RNA sequence, it is necessary that a given RNA or DNA molecule must be delayed but not completely blocked or otherwise deactivated by the dissolvable barriers. For example, in some cases the detection mechanism of a diagnostic device provided herein requires that an RNA sequence interact with a toehold-switch-containing RNA structure to, thus, regulate an enzyme (e.g., beta-galactosidase) that will interact with a substrate to produce the desired color change. To evaluate the barrier's ability to accommodate these requirements of a target RNA sequence, the delay times of an RNA molecule passing through the barriers can be measured.

In other cases, the detection mechanism employs a fluorescent broccoli-RNA/dye complex. In such cases, the bottom layer of a multilayer device is treated with a dye that only fluoresces when in contact with a particular RNA structure. For time-delay, sucrose treated wells can be placed on top of the dye-treated layer, along with one more untreated layer of paper on top of the sucrose layer. The RNA structure is then dropped onto the top wells of the device, which is then incubated in a plate reader at 37° C. to allow for detection and measurement of fluorescence in the bottom layers.

In some cases, it may be advantageous to additionally employ lateral flow to distribute small molecular weight reaction products (e.g., nucleic acids) following amplification. For example, microfluidic layers patterned using hydrophobic wax inks within the device can be used to distribute reaction products laterally, so that multiple agents can be detected simultaneously and products can be combined as computational inputs. Importantly, the sample will be driven through the device purely through capillary forces and employ reactions that are active at ≤37° C. Examples of potential reactions include recombinase polymerase amplification, cell-free protein expression, and in vitro transcription using RNA polymerases such as T7, SP6, and T3. As a result, the diagnostic can be run with minimal human intervention and employ patient body heat for power. The use of transverse flow means that the devices do not require much lateral area, so that it will be possible to run dozens of tests within a single business-card-sized diagnostic system. Existing commercial tests often employ lateral flow methods to report assay results in which capillary forces carry the analyte across a device. For example, the existing Zika diagnostic test requires multiple liquid handling steps and incubation at more than one temperature (FIG. 1A), which complicates its deployment in the field. In addition to liquid transfer steps, separate reactions must be carried out for well-defined times. Lateral flow, however, requires transport distances of approximately 1 cm and thus takes up considerably more device area compared to the diagnostic devices provided herein that are based on transverse flow. By using a transverse flow configuration rather than a lateral flow configuration, the devices require less lateral area and more tests can be provided in the same area. In addition, the lower assay footprint can be used to shrink test size and facilitate panel-based tests.

After capillary forces facilitate transfer of amplification products within the device for reporter reactions, assay results can be read out from the bottom (or lowest layer in FIG. 1B) set of reactions using, for example, a reader (e.g., a plate reader or a custom smartphone app). In some cases, the device is used with a reader that is external to the diagnostic device. In other cases, it may be advantageous to incorporate a reader into the diagnostic device itself. By way of example, an external reader can be a portable electronic reader. In this manner, the electronic reader serves as companion technology that provides robust and quantitative measurements of device outputs. An exemplary electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between an LED light source (570 nm) and electronic sensors. Using onboard electronics, samples can be read at a rate of 29 reads per minute. Accordingly, the portable electronic reader provides low-noise measurements of changes associated with the reporter element including changes in light transmission due to LacZ-mediated color change.

Figure 2:
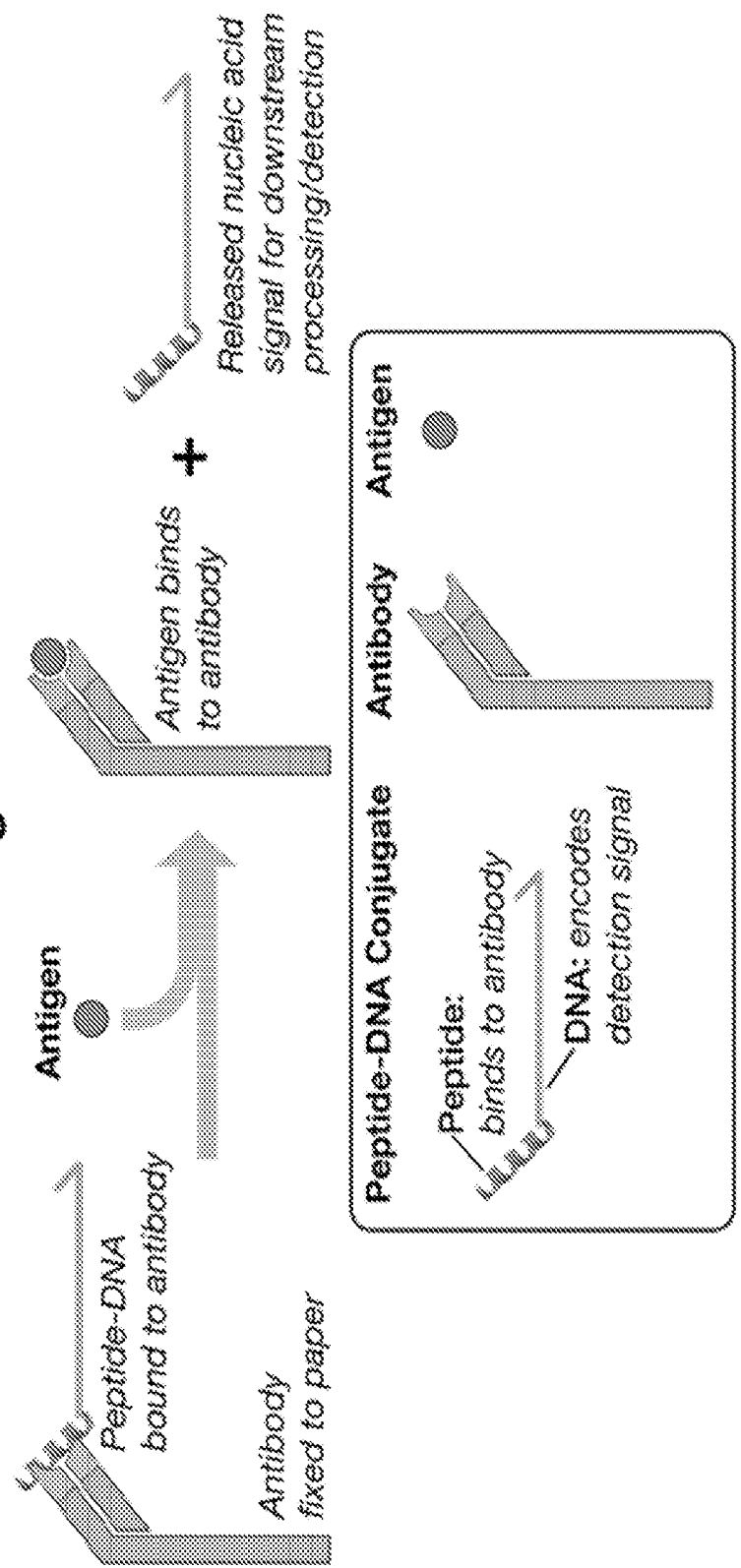
FIG. 2 is an illustration of an antigen detection scheme based on displacement of peptide-DNA conjugates. A peptide-DNA conjugate with a peptide sequence derived from a known antigen epitope for an antibody is used to partially block the antigen binding site of an antibody. The antibody is fixed to the paper substrate. Addition of the antigen causes the peptide-DNA conjugate to be displaced from the binding site of the antibody. The released peptide-DNA conjugate can then be used in downstream information processing or detection reactions.

Protein Detection via Peptide-DNA Conjugates: While pathogen nucleic acids can be readily interfaced with RNA-based sensors like toehold switches, doing the same for protein detection is considerably more challenging. As shown in FIG. 2, peptide-DNA conjugates are used in the integrated devices provided herein to convert protein binding into a DNA signal that can be detected by a biomolecular computing system. In some cases, capture antibodies known to bind to a target antigen are affixed to paper tests using well established methods. Peptide-DNA conjugates having peptide sequences that match or that are similar to those of the antigen are then used to bind to and partially block binding sites of the capture antibodies. When a sample is contacted to the diagnostic device, any antigens present in the sample will displace the relatively weakly held peptide-DNA conjugates and enable them to reach the biomolecular computing regions of the device for detection. Since the peptide-DNA conjugate detection scheme employs antibodies for detection, the devices will detect any antigen recognizable by an antibody. The range of analytes can be extended to carbohydrates and glycoproteins, nucleic acid tertiary and secondary structures, methylated DNA/RNA, lipids, and small molecules, among others. The sole requirement is for there to exist a peptide that binds to the antigen-binding site and can be displaced by the target analyte. Such peptides can be identified through known antigen epitopes or by exposing the antibody to arrays of peptide sequences and determining the locations in which the antibody binds. The capture array could then be exposed to the analyte to identify those peptides that can be displaced by the analyte. Although the above discussion references peptide-DNA conjugates only, peptide-RNA and peptide-dsDNA (double-stranded DNA) conjugates can also be used in the detection scheme. In addition, an RNA or DNA aptamer that binds to the antibody could also be used to replace the peptide component of the system. Antibodies can be detected using capture antibodies, antigens, or peptide epitopes that bind to the antibody of interest. In such cases, a peptide-DNA conjugate would initially be bound to the capture peptide epitope prior to its displacement. The sequence to use for the peptide of the peptide-DNA conjugate can be obtained using the peptide-array approach described above.

Figure 3:
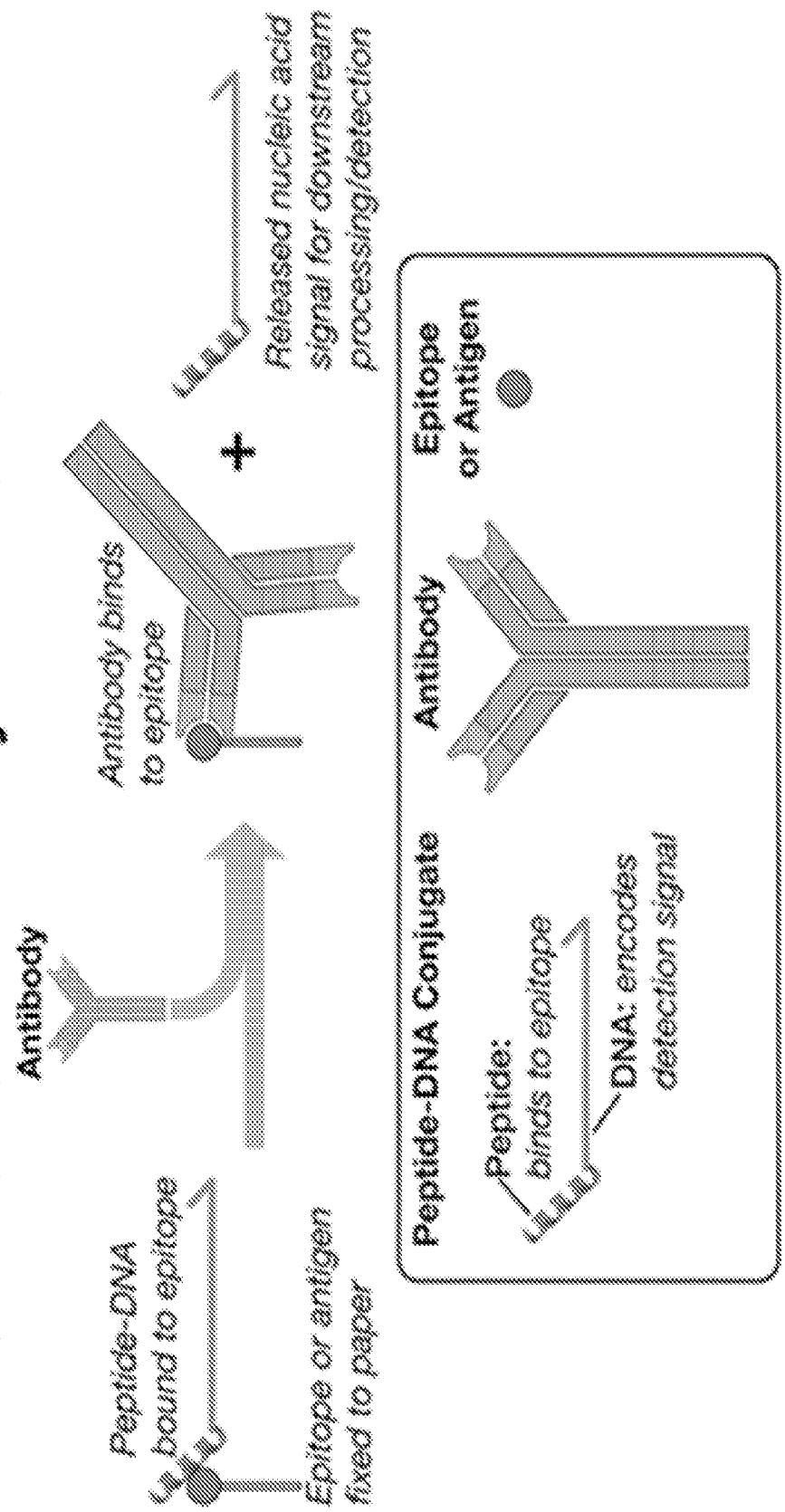
FIG. 3 is an illustration of an antigen detection scheme based on displacement of peptide-DNA conjugates. A peptide-DNA conjugate with a peptide that binds an antigen epitope for the target antibody is used to partially block the epitope. The antigen or epitope is fixed to the paper substrate. Addition of the antibody causes the peptide-DNA conjugate to be displaced from the epitope. The released peptide-DNA conjugate can then be used in downstream information processing or detection reactions. The sequence of the peptide in the conjugate can be determined from screens involving binding of the antigen to peptide arrays.

As shown in FIG. 3, a diagnostic device can be configured to detect antibodies of interest. In general, a peptide-DNA conjugate is bound to an epitope or antigen fixed to a paper layer. In the presence of sample containing the antibody of interest, the antibody displaces the relatively weakly held peptide-DNA conjugate. In this manner, the peptide-DNA conjugate is released in the presence of antibody of interest and can reach the biomolecular computing regions of the device for downstream processing and detection.

Figure 4:
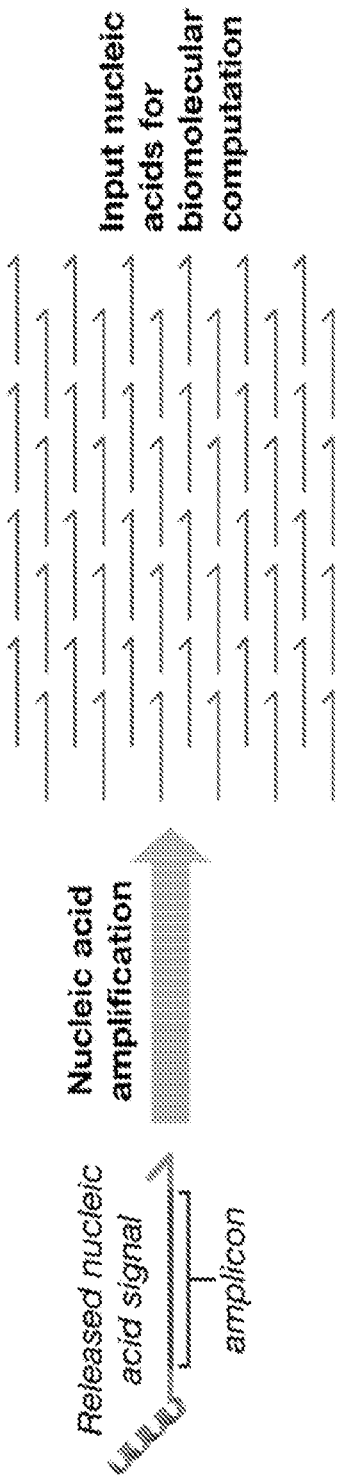
FIG. 4 illustrates amplification of a protein detection signal via nucleic acid amplification. Upon release of the peptide-DNA conjugate from its cognate antibody or epitope, the conjugate can pass through to the amplification regions of the device. The nucleic acid component of the conjugate can then be amplified using isothermal reactions to generate millions to billions of copies of the internal amplicon sequence. These amplified nucleic acids can be used as inputs for downstream information processing in other regions of the device.

The devices provided herein are capable of protein detection with enhanced sensitivity. For example, application of isothermal amplification schemes such as recombinase polymerase amplification (RPA) and nucleic acid sequence-based amplification (NASBA) could enable PCR-like sensitivity to be achieved for protein detection. Referring to FIG. 4, isothermal amplification can be employed to amplify copies of DNA or RNA of a released peptide-nucleic acid conjugate. Isothermal amplification reactions generally comprise one or more enzymes that disrupt base pairing in double-stranded DNA templates to allow primers, displacers, and/or blockers to bind to exposed single-stranded DNA regions. In certain embodiments, the isothermal nucleic acid amplification technique is Recombinase-Polymerase Amplification (RPA), which is a method for the amplification of target nucleic acid polymers without the need for thermal melting of double-stranded templates. RPA employs polymerases (DNA polymerases or polymerase complexes capable of strand displacement) to generate copies of template nucleic acid molecules. It is a necessity of most nucleic acid polymerases that incorporation requires a free 3'-hydroxyl moiety on the terminal sugar of a short stretch of double-stranded nucleic acid adjacent to the site of new synthesis. This stretch of double-stranded nucleic acid is typically formed on a template by a short complementary sequence, called a primer, which serves as an initiation site for the polymerase synthesis reaction. Typically, for in vitro reactions the primer is supplied as a short, often chemically synthesized, single-stranded DNA (or modified DNA or RNA), and is usually referred to as an oligonucleotide primer. For the methods provided herein, primers can be designed to specifically target a gene of interest such as a gene of a particular pathogen or a cancer marker.

The ability of RPA to discriminate between target and non-target DNA and amplify only target sequences is a key aspect of improved sensitivity. For the purposes of this disclosure, each of the terms "target" and "non-target" can refer to a wild-type or mutant (e.g., SNP-containing) nucleic acid molecule, depending on the intended target. For example, the target may be a SNP-containing nucleic acid molecule if the method is employed to detect the presence of a SNP in a sample. Any isothermal amplification protocol can be used. For example, other isothermal amplification methods include NASBA (nucleic acid sequence-based amplification), loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), and single primer isothermal amplification (SPIA).

The terms "detect" or "detection" as used herein indicate the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

As used herein, a "sample" means any material that contains, or potentially contains, which could be infected or contaminated by the presence of a pathogenic microorganism. Samples appropriate for use according to the methods provided herein include biological samples such as, for example, blood, plasma, serum, urine, saliva, tissues, cells, organs, organisms or portions thereof (e.g., mosquitoes, bacteria, plants or plant material), patient samples (e.g., feces or body fluids, such as urine, blood, serum, plasma, or cerebrospinal fluid), food samples, drinking water, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples. In other embodiments, the methods provided herein are used for anti-counterfeit applications, such as confirming that pharmaceuticals are genuine or confirming the identity of high value items that have been fabricated or are known to contain specific nucleic acid species.

Figure 5:
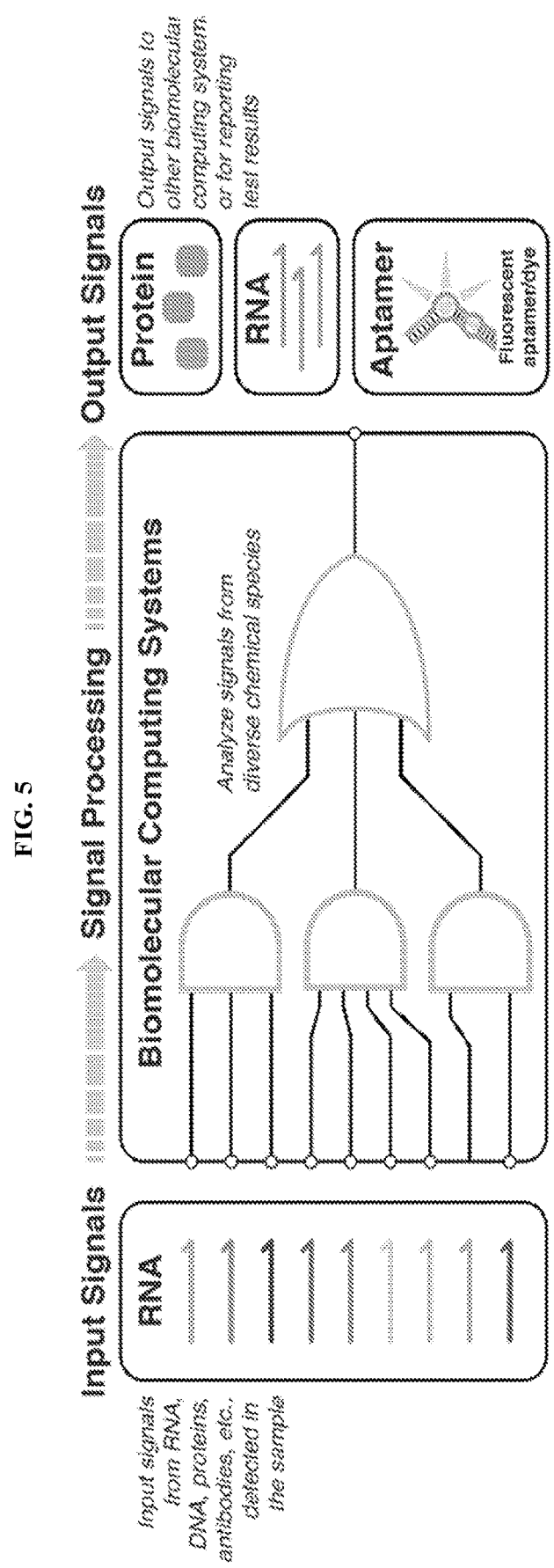
FIG. 5 is a schematic illustration of the biomolecular computing system. Input signals in the form of RNA (or DNA) are acted on by the computing system. Input signals are generated by RNA, DNA, proteins, antibodies, and carbohydrates in the biological sample and are detected and amplified in different upstream device layers. The biomolecular computing systems employ nucleic acid interactions to perform molecular logic based on the requirements of the diagnostic. Upon completion of the computation, the result is output in the form of protein (e.g., lacZ, GFP, or an RNA polymerase), RNA, or an aptamer. In some cases (e.g., GFP or aptamer), the output signal is a reporter that displays the diagnostic test result. In other cases (e.g., RNA or RNA polymerase), the output signal can be used in a downstream biomolecular computing layer.

Multi Analyte Processing Using Embedded Biomolecular Computing Systems:

Following detection according to a scheme described herein, signal from the protein analyte can be converted into a nucleic acid signal that can be processed using nucleic-acid-based biomolecular computing systems. These systems can act on signals generated from proteins and from those generated by nucleic acids present in the original biological sample as illustrated schematically in FIG. 5. Referring to FIG. 5, input signals in the form of RNA (or DNA) are generated by RNA, DNA, proteins, antibodies, carbohydrates, and lipids in the biological sample and are detected and amplified in different upstream device layers, then acted on by a biomolecular computing system that employs nucleic acid interactions to perform molecular logic based on the requirements of the diagnostic.

Upon completion of the computation, the result is output in the form of protein (e.g., lacZ, GFP, or an RNA polymerase), RNA, or an aptamer. In some cases, the output signal is a reporter (e.g., GFP or aptamer) that displays the diagnostic test result. In other cases, the output signal is RNA or RNA polymerase that can be used in a downstream biomolecular computing layer.

In some cases, the output is in the form of a reporter protein, e.g., a polypeptide with an easily assayed enzymatic activity or detectable signal that is naturally absent from a host cell. Exemplary but non-limiting reporter proteins include lacZ, catalase, xylE, GFP, RFP, YFP, CFP, neomycin phosphotransferase, luciferase, mCherry, and derivatives or variants thereof. In some embodiments of any of the aspects, the reporter protein is suitable for use in a colorimetric assay. Examples of genes encoding fluorescent proteins that may be used in accordance with the invention include, without limitation, those proteins provided in U.S. Patent Application No. 2012/0003630 (see Table 59 therein), incorporated herein by reference.

In some cases, the biomolecular computing system is an RNA-based biomolecular device that we have recently developed to perform logic operations. Such 'ribocomputing' systems (i.e., RNA-based biomolecular computing systems) comprise de novo designed RNA parts and operate via predictable Watson-Crick base-pairing rules, enabling effective in silico design of devices with prescribed functions. Ribocomputing systems detect input RNA molecules and use them to compute a user-defined logic expression. If the expression is satisfied, the devices synthesize a desired protein as output. This protein can be a reporter enzyme, which can display the results of a diagnostic test, or it can be an RNA polymerase, which can synthesize an output RNA for a downstream ribocomputing element. To date, ribocomputing elements have been limited to use in living cells (Green et al., Nature 548:117-121 (2017)). However, in some cases, the devices and systems provided herein are configured for use in paper-based cell-free systems such that they can be used for diagnostic purposes.

Although we reference here ribocomputing devices based on toehold-mediated strand displacement reactions and protein outputs (Green et al., Nature 548:117-121 (2017)), it should be understood that multiple alternative biomolecular computing systems can be used instead. Other potential systems for implementing biomolecular computing in the diagnostics include loop-mediated riboregulator logic systems, near-threshold translational repressor systems, aptasensor systems based on aptamers such as Broccoli, or combinations thereof. In all these systems, RNA base pairing interactions can be used to evaluate logic expressions to determine if a biological sample has the specific combination of characteristics indicative of infection by a pathogen or a particular disease (e.g., cancer). Also the biomolecular computing system can be as simple as a single riboregulator that detects a released peptide-DNA conjugate or the amplified RNA product thereof. In this case, the computing system would only evaluate the simple IF/THEN expression "IF RNA A, THEN translate gene B".

In some cases, the peptide-DNA conjugate detection scheme is used to detect a variety of known antigens through knowledge of common epitopes or by screening them on peptide arrays. By way of example, peptides that detect prostate specific antigen (PSA) can be designed to provide a high degree of binding affinity to PSA antibodies and low DNA signal leakage while maintaining efficient release upon antigen binding. In other cases, the peptide-DNA conjugate detection scheme is used with panel of mosquito-transmitted flaviviruses, which include Zika virus, dengue, chikungunya, and yellow fever. Zika is difficult to detect via nucleic acid testing outside of the acute phases of infection, even though it can still be transmitted sexually. Furthermore, Zika is notoriously difficult to distinguish from dengue using conventional antibody-based tests due to their similar immune responses. Thus, a multi-factorial test that detects the levels of multiple antibodies and nucleic acids before making a diagnosis provides an advanced diagnostic for a panel of closely related flaviviruses. Similarly, the diagnostic devices provided herein can be used to identify subjects having particular single nucleotide polymorphisms (SNPs) to, for example, stratify subjects in clinical studies. In other cases, the diagnostic devices provided herein can be used to acquire large data sets for understanding, for example, the spread of infectious diseases in a community.

Designing Sequence-Specific Integrated Devices and Systems:

The sequence-specificity of the diagnostic devices provided herein means that they can be used for various DNA testing applications. For example, the integrated devices described herein provide a very inexpensive sequence-specific device for detection of oncogenes via known SNPs (e.g., detecting BRCA1 and BRCA2 oncogenes in a patient sample). Other applications for sequence-specific devices include, without limitation, detecting antimicrobial drug resistance and detecting infection of various pathogens (e.g., viruses, bacteria, parasitic organisms, etc.). For example, detection of single-nucleotide differences can be used to identify individuals of interest with high confidence. This capability, particularly when implemented in a low-cost and portable format, could be useful for law enforcement, forensics, and as part of biometric security measures.

Field Applications of Integrated Devices for Conservation Efforts:

In some cases, it may be advantageous to use integrate diagnostic devices as provided herein in the field to guide a variety of wildlife conservation efforts. For example, integrated devices can be rapidly deployed in non-laboratory settings for DNA-based identification of endangered species and for acquiring large data sets for understanding species diversity in a particular region. In addition, the integrated devices can be used in customs offices, for example, to ensure that wildlife crossing the border is not infected with viruses or fungi whose import could be harmful to the indigenous wildlife.

Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLES

Example 1—Establishing Consistent Fluidic Delay Times

The sample to enter and flow through the proposed paper-based devices is an aqueous solution comprised of a variety of molecules and macromolecules, with one of the latter substances being the target RNA or DNA sequence that requires isolation and amplification. A time-sensitive barrier will impact each of these substances differently, with some moving through the barrier faster or slower than others. However, most if not all of these various substances will not advance faster than the water carrying them. Therefore, in order to assess the ability of the fluidic barriers to block the passage of fluid, the barriers will be evaluated for their ability to delay the advance of a water sample containing a low-molecular weight food color dye for visible detection.

Figure 6:
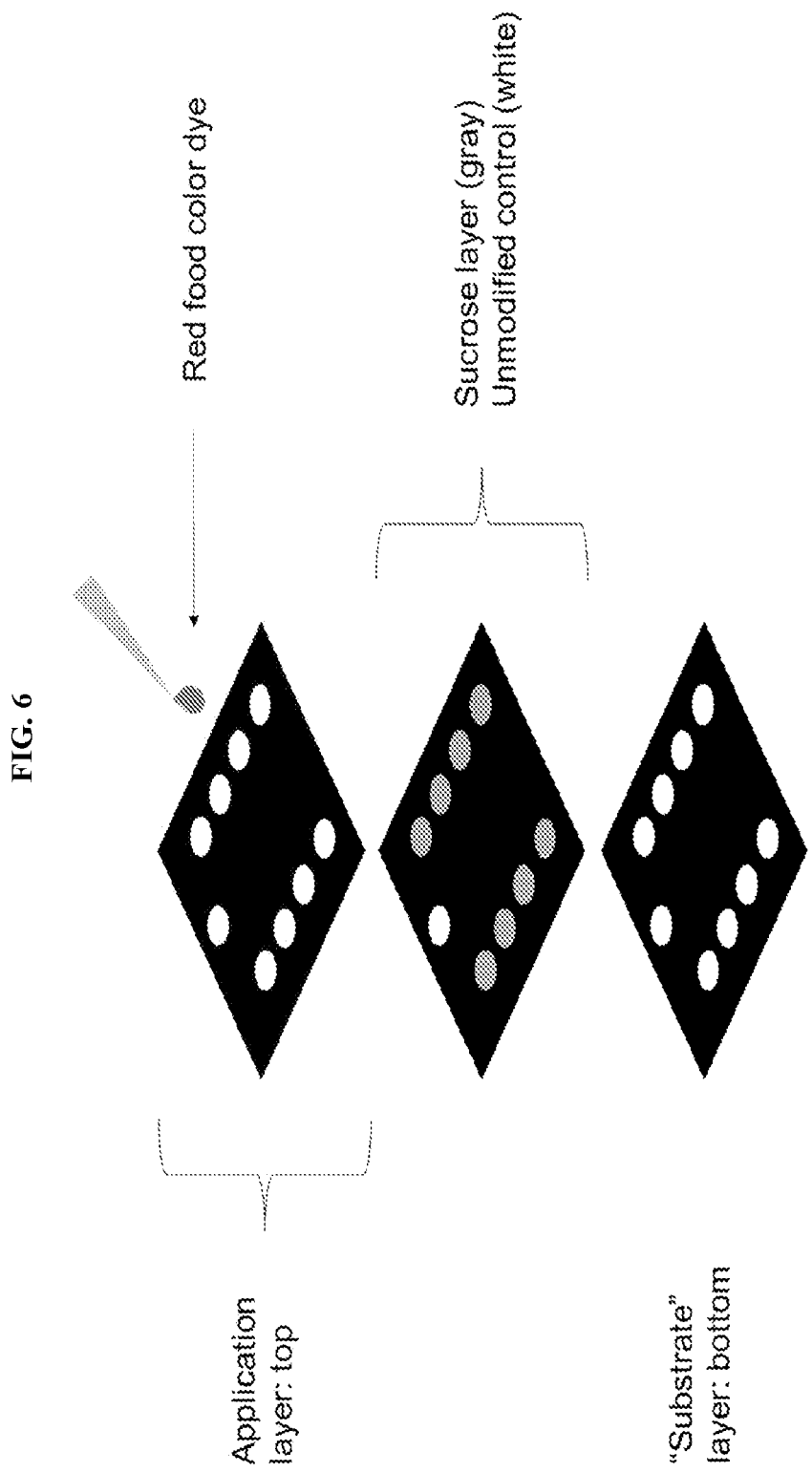
FIG. 6 illustrates a device configuration for evaluating fluid barrier delays of aqueous solutions.

To do this, we designed the setup shown in FIG. 6. The setup consists of three layers, one of which has selected wells treated with different concentrations of sucrose solution or another water-soluble compound, such as methyl cellulose or pullulan. For these experiments, the wells are treated by simply applying a drop of the sucrose solution and allowed to dry. The bottom and top layers are untreated. When a solution of food color dye is added to the top layer wells, it can travel through the top layer, be inhibited by the sucrose-treated wells in the middle layer, and finally cause a color change to be observed in the bottom layer. The amount of time between dropping the liquid onto the top layer and the appearance of a visible color change on the bottom layer can then be measured.

We have successfully demonstrated that we can delay fluid flow through the 3-layer system with the addition of a sucrose-treated middle layer, and that, by varying the concentration of sucrose solution, we can control how long fluid is delayed from reaching the bottom layer. Using a 20% sucrose solution, we measured 6±1 minutes delays in liquid passage. Using a 30% sucrose solution, the delay was extended to 12±3 minutes. We expect that higher sucrose solution concentrations and repeated applications of the sucrose will enable delays of longer periods to be obtained. Furthermore, additional delay layers can also be added between the top and bottom layers in order to provide further control over sample passage. In addition to sucrose, we also studied methyl cellulose and pullulan as transient layers. These compounds also successful delayed fluid flow through the layered devices. Thin films of methyl cellulose added between top and bottom paper-based microfluidic layers were also successful at delaying fluid passage.

Verifying Enzyme Function after Interacting with Delay Material

The output of the detection layer in the final device is a color change produced from the enzyme beta-galactosidase interacting with a substrate. The sample solution will become more concentrated with sucrose, or more generally the barrier compound, as it dissolves each barrier layer. The increased concentration of sucrose may affect the interaction between the enzyme and substrate and in turn the final readout of the device. Therefore, it is important to test the viability of the enzyme-substrate interaction on paper in a concentrated sucrose solution. To test this, the same 3-layer setup as shown in FIG. 6 was used, but with the bottom layer wells having been treated with chromogenic substrate chlorophenol red-β-D-galactopyranoside, and a solution of enzyme beta-galactosidase as the solution to be added to the top layer. The middle layer wells were treated with different concentrations of sucrose in the same manner as before.

Figure 7:
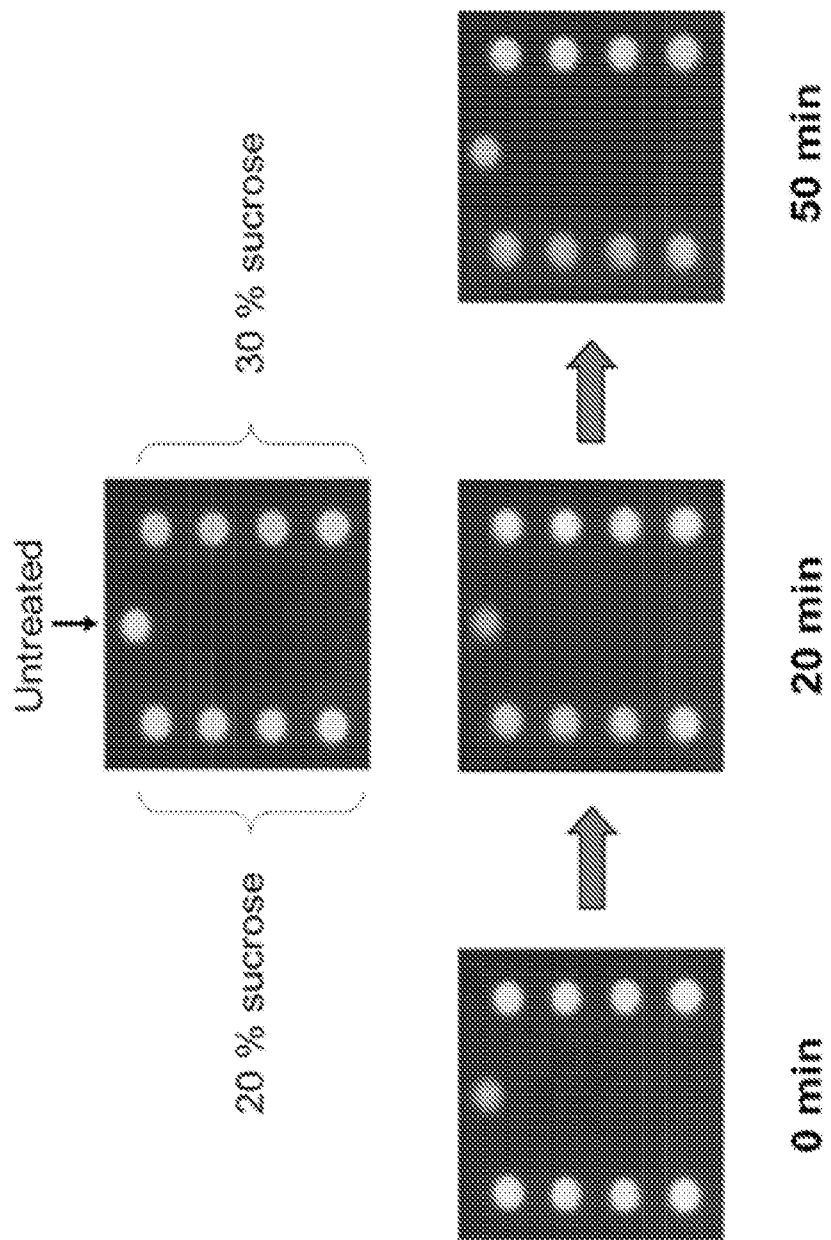
FIG. 7 demonstrates results of adding enzyme to sucrose barriers within a 3-layer device. A yellow to purple color change is seen in both the 20% sucrose and 30% sucrose barriers within the middle layer of the device.

As shown in FIG. 7, a color change from yellow to purple was observed for the both the 20% and 30% sucrose-treated devices, indicating that the enzyme successfully interacted with the substrate on paper even in concentrated sucrose solutions. An important observation here is that it took longer for a color change to occur in this device than in the previous device, where the color change was not dependent on large protein-sized molecules clearing the barrier. A similar increased delay time for a molecule like RNA is expected in the future tests.

Quantifying Delay Times for RNA or DNA Sample

Since the target analyte for the detection layer is an RNA sequence, it is necessary that a given RNA or DNA molecule must be delayed but not completely blocked or otherwise deactivated by the dissolvable barriers. The detection mechanism outlined in the proposed device requires an RNA sequence to interact with a toehold switch-containing RNA structure, regulating an enzyme (e.g., beta-galactosidase), which will then in turn interact with a substrate to produce the desired color change. To evaluate the barrier's ability to accommodate these requirements of a target RNA sequence, the delay times of an RNA molecule passing through the barriers will be measured.

In one example, the test utilizes a fluorescent broccoli-RNA/dye complex. A similar setup as described for the previous steps is used. A dye that can only fluoresce when in contact with a particular RNA structure is used to treat the bottom layer of a multilayer setup. Sucrose treated wells are placed on top of the dye-treated layer along with one more untreated layer of paper on top of the sucrose layer. The RNA structure is then dropped onto the top wells of the device, which is then be incubated in a plate reader at 37° C. to allow the fluorescence of the bottom layers to be measured. It is expected that the sucrose treated 3-layer setups would yield a slower fluorescence response than those that were untreated.

Quantifying Delay Times for Processed RNA Target and Full Detection Layer

The final step involves fabricating a similar 3-layer device as described previously, except with the detection layer being treated with the full RNA-based detection system that will be used in the proposed device. The middle layer is treated with sucrose as before, but the target will be the RNA sequence that will activate the toehold switch located in the detection layer and produce the protein via expression, which will then interact with the substrate and produce the desired color change. In summary, the final step involves timing target RNA flow and colorimetric output under the conditions of the actual device.

Example 2—Using DNA-Peptide Conjugates to Activate Toehold Switches

This section describes assays performed to develop an improved integrated diagnostic device and system which integrates a peptide-displacement system for protein detection with the amplification and multiplexing capabilities of nucleic acid-based systems for amplification, signal processing, and readout. Critical to this integrated system is the use of DNA-peptide conjugates to bridge the gap between protein and nucleic acid capabilities in synthetic networks. Using a DNA-peptide conjugate as the cognate trigger to activate a toehold switch, our hybrid system is a paper-based diagnostic device that hosts two spatially separated reactions: a protein detection reaction employing peptide displacement and a nucleic acid detection reaction employing a toehold switch. Given the complexity of the final integrated diagnostic, we have focused initial research on three critical components that are crucial for proper function of the diagnostic: (1) Incorporation of peptide-DNA trigger conjugates into cell-free toehold switch reactions, (2) PCR Amplification with DNA-peptide conjugates, and (3) Implementation of peptide displacement reactions in paper test strips.

Figures 8A, 8B, 8C:
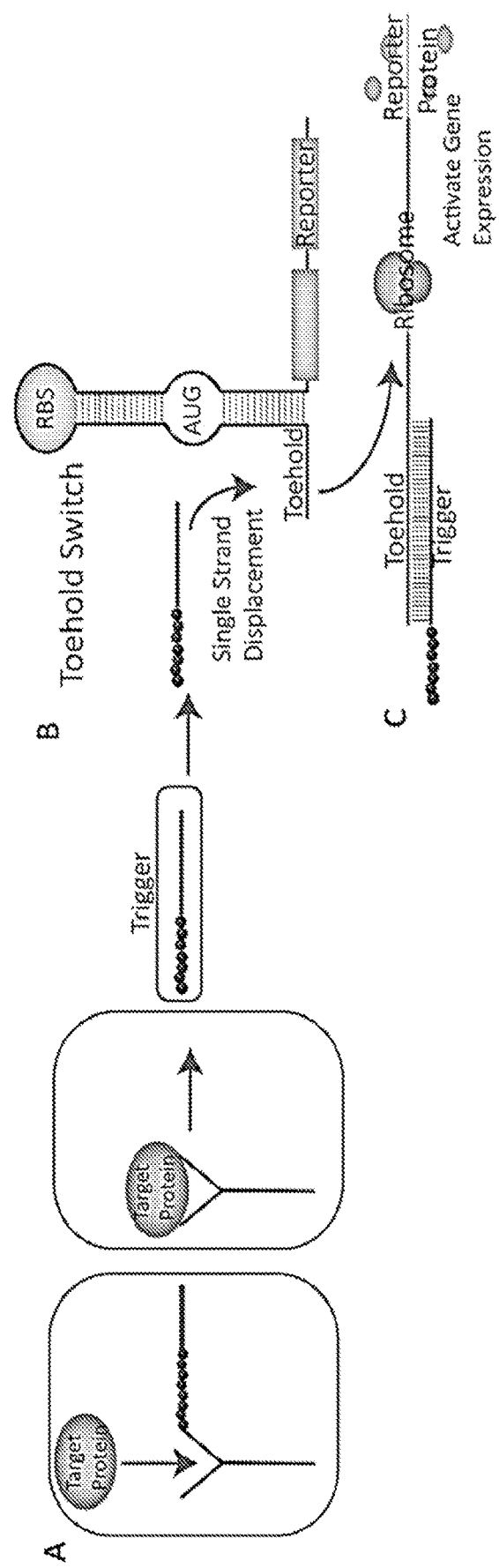
FIGS. 8A-8C illustrate protein activation of toehold switch. A. DNA-peptide trigger remains bound to antibody. In presence of target protein, trigger is displaced. B. Trigger then flows down to toehold switch, initiating strand displacement. C. Translation occurs and reporter protein is produced.

Referring to FIG. 8A, a DNA-peptide conjugate binds to the target antibody to provide a downstream DNA signal. While the DNA-peptide conjugate is bound, the toehold switch reaction lacks its trigger sequence and thus remains inactivated (FIG. 8B). In the presence of a target protein, the DNA-peptide trigger will be displaced and move by capillary forces to a toehold switch cell-free reaction thereby activating translation of the reporter gene (FIG. 8C). Importantly, by converting peptide binding into a DNA output signal, it is possible to simultaneously identify multiple proteins using the sequence-specificity of different toehold switches. Moreover, DNA signals can be readily processed using nucleic acid logic circuits so that a positive test result is only reported when specified combinations of different proteins are detected. Lastly, easy-to-implement isothermal amplification reactions can be deployed in the test strip device to decrease the detection limit to enable highly sensitive detection of different proteins. With the great importance of protein-protein interactions in biology, our synthetic biomolecular networks can be used for more robust and widely applicable hybrid protein/nucleic acid diagnostics.

Experimental Results

1) Incorporation of Peptide-DNA Trigger Conjugates into Cell-Free Toehold Switch Reactions:

To explore the ability of a DNA-peptide conjugate to link protein and nucleic acid detection, we first needed to confirm that the peptide component of the conjugate would not inhibit interactions between the trigger DNA and toehold switch and ultimately enable toehold switch activation. A previously reported second-generation toehold switch, FER1_H16, was used as the output riboregulator for this study because of its high ON/OFF ratio of over 400-fold when paired with its cognate trigger experimentally (Green et al., Cell 2014. 159, 925-939). To construct the DNA-peptide conjugate, 5' amino-modified FER1_T16, which contained the cognate trigger sequence of FER1_H16, was reacted with N-hydroxysuccinimide-sulfo-dibenzylcyclo octyne. The modified trigger was then conjugated to a peptide containing an azido lysine using copper-free click chemistry to form the DNA-peptide conjugate. Peptides used for conjugation include the prostate specific antigen peptide from Francione et al. (RSC Adv. 2015. 5, 6595-6598), a streptavidin binding peptide, and an alpha tubulin peptide DM1A. Streptavidin binding peptide (SBP) was selected as a target peptide because of its ability to bind streptavidin with a dissociation constant of 2.5 nM, indicating it would bind streptavidin with a high binding affinity but could still be displaced by biotin (Keefe et al., Protein Expression and Purification. 2001. 23, 440-446). Peptide sequences used are found in Table 1.

TABLE 1

Sequences of Peptides and DNA Triggers Used

| | |
|---|---|
| PSA peptide | H-DVCAQV-NH$_2$ (SEQ ID NO: 1) |
| Streptavidin Binding Peptide | MDEKTTGWRGGHVVEGLAGELEQLRARLEHHP QGQREP (SEQ ID NO: 2) |
| FER1_T16 DNA trigger sequence | 5' GCA GAA ACT AAC AGA AGC CAA ATC AAT TAC ATA CTA 3' (SEQ ID NO: 3) |
| DM1A peptide | AALEKDY (SEQ ID NO: 4) |

Figure 9:
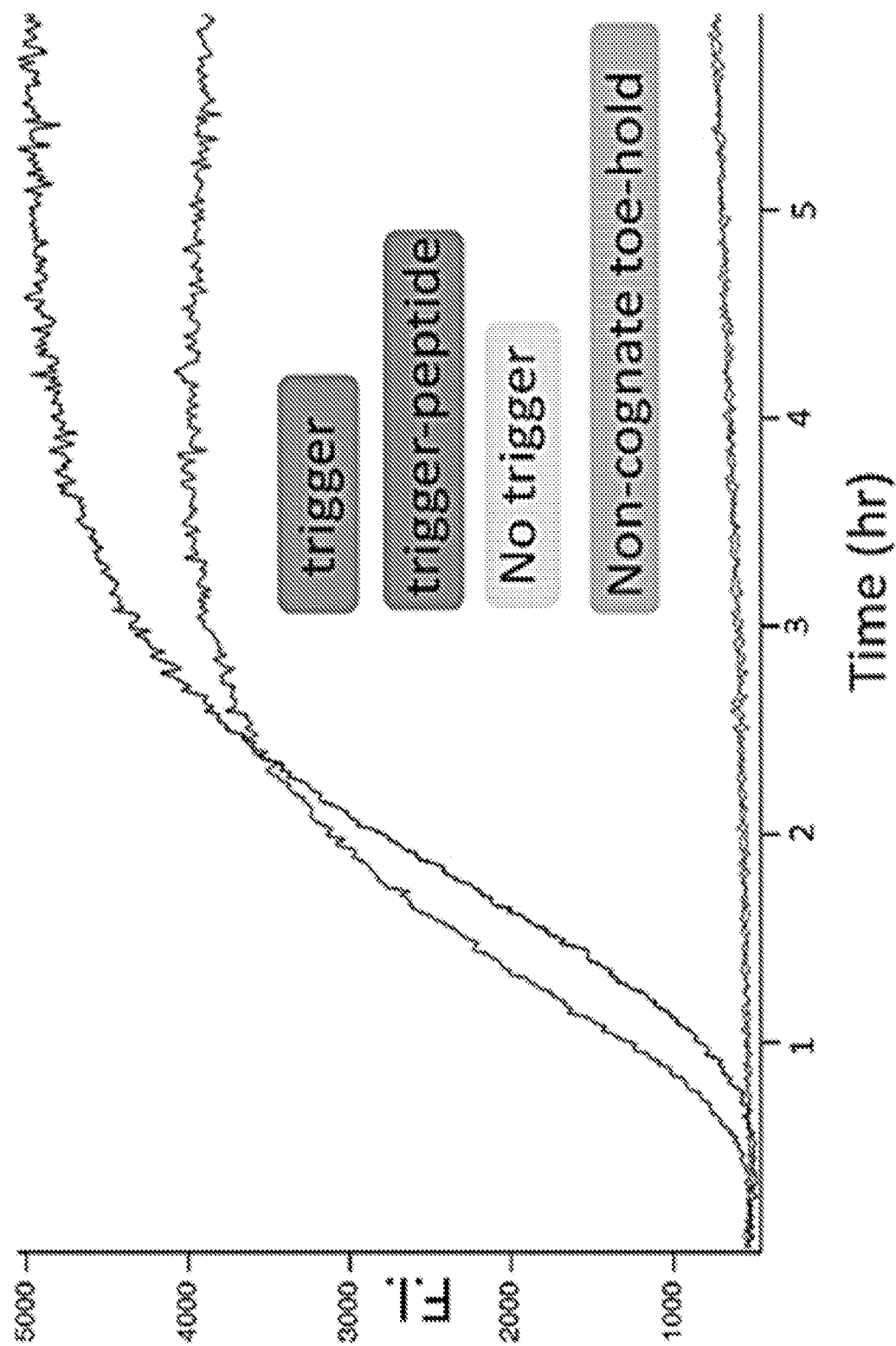
FIG. 9 is a graph demonstrating DNA-peptide (PSA) conjugate toehold activation. The DNA trigger (blue) shows highest activation of cognate toehold switch. Peptide-conjugated DNA trigger (purple) also activates cognate toehold. Green shows toehold in presence of no trigger, signaling no activation. Gray demonstrates trigger-toehold specificity, with no activation from DNA-peptide trigger with a non-cognate toehold switch.

To test for toehold activation, the peptide-DNA conjugates were combined with FER1_H16 toehold constructs in a cell free reaction following the In Vitro Protein Synthesis protocol from the PURExpress™ system (New England BioLabs). This system contains all enzymes and components required for transcription and translation outside of a cell. To monitor toehold switch activation, the reporter LacZ gene or green fluorescent protein (GFP) was incorporated downstream of the FER1_H16 hairpin module. Chlorophenol red-β-D-galactopyranoside, a substrate that when cleaved by β-galactosidase results in dark purple color, was used to visualize the production of β-galactosidase from the LacZ gene. A plate reader was used to measure the absorbance of chlorophenol red-β-D-galactopyranoside at 570 nm for LacZ over a 6-hour period. GFP was measured by fluorescence intensity at 475 nm (FIG. 9).

Several peptides with different lengths and compositions were also tested for toehold activation. No discernable differences in toehold activation were found. Reporter genes for mCherry were also incorporated into toeholds with successful translation upon toehold activation. From these results, we conclude that peptide-conjugated nucleic acids can efficiently activate toehold switches in cell-free reactions. Although toehold switches were used for experiments, a wide array of different riboregulators or RNA-based switches should be compatible with DNA-peptide conjugates, including loop-mediated riboregulators, translational repressors, ultraspecific riboregulators, and aptasensors.

2) PCR Amplification with DNA-Peptide Conjugate:

To understand the capacity of DNA-peptide conjugates to bridge this gap between proteins and nucleic acids, we next investigated whether the conjugates could successfully be used as amplification primers and templates. The ability to use DNA-peptide conjugates in typical amplification reactions has three important implications for their application in diagnostic systems:

(A) Amplification of protein detection signals: After displacement of the peptide-DNA by the target analyte, the displacement signal can be amplified using a technique such as PCR or an isothermal amplification method such as RPA or NASBA. For such an amplification to be successful, a target template with a covalently bound peptide must be compatible with the reactions. Nucleic acid amplification methods can in principle dramatically lower the detection limit of protein detection to enable identification of low copy number proteins.

(B) Simple and low-cost preparation of double-stranded DNA (dsDNA)-peptide conjugates: Using a DNA-peptide conjugate that contains the DNA sequence of a universal primer enables a peptide to be conjugated to a diverse array of different dsDNAs that can be used to activate different riboregulators in the readout phase of the diagnostic test. In this approach, two libraries would be used: a library of different peptides conjugated to a universal amplification primer, and a DNA library of different riboregulator trigger cassettes containing a promoter, a trigger sequence, and common sites for priming. With these two libraries and PCR amplification, a large library of peptides conjugated to specific dsDNA trigger cassettes can be generated to facilitate highly multiplexed tests.

(C) Transcription-based amplification of protein detection signals: dsDNA-peptide conjugates produced by PCR or another amplification method have the capacity to be transcribed to generate multiple RNA copies for detection by a riboregulator. In addition, the single-stranded form of the transcribed RNA will enable facile detection by a riboregulator and exploit the stronger thermodynamics of RNA-RNA binding compared to RNA-DNA binding. Thus, dsDNA-peptide conjugates that are transcribed can lower the detection limit of protein identification and simplify the assay.

Figure 10:
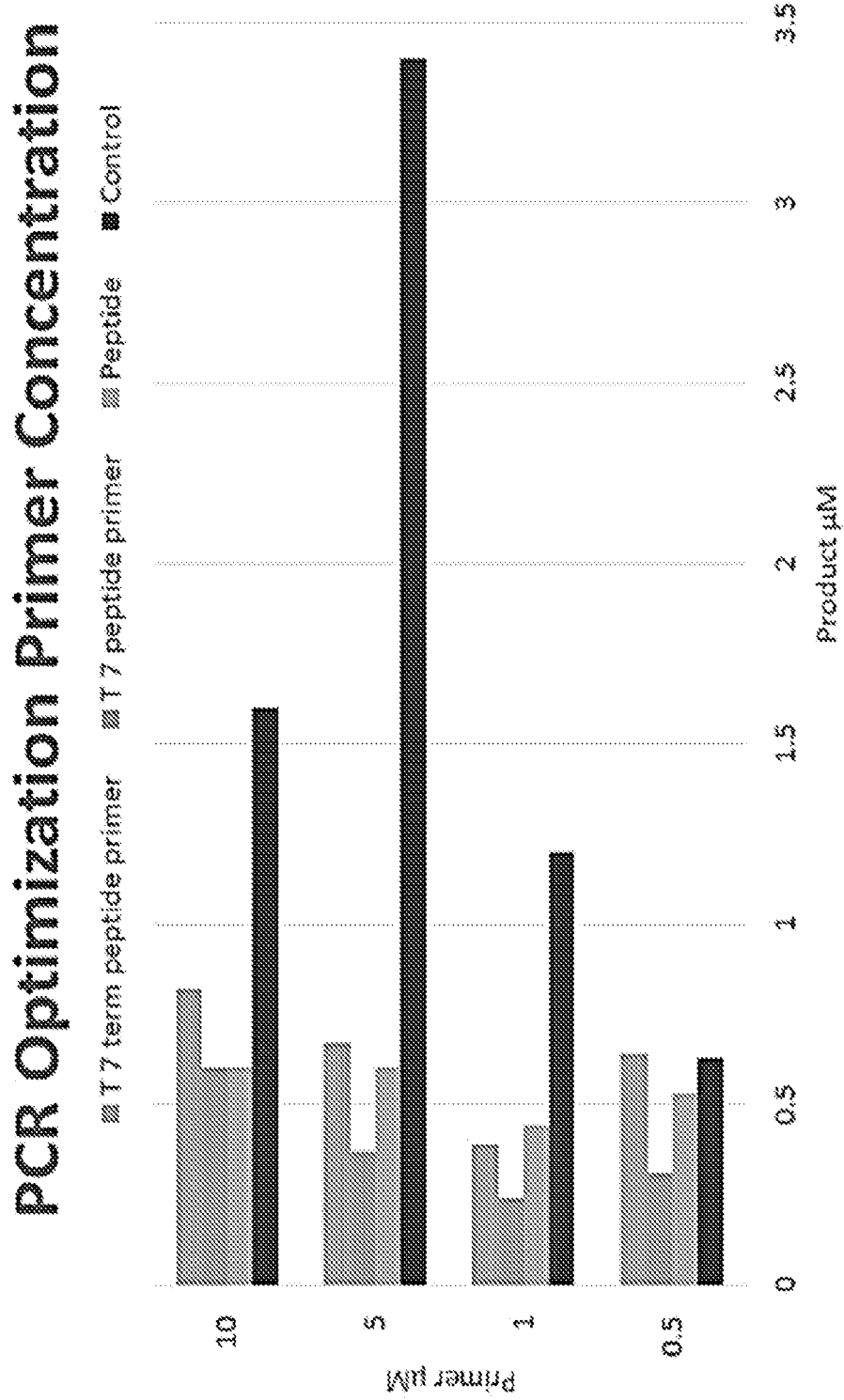
FIG. 10 demonstrates PCR optimization. PSA peptides were conjugated to either T7 forward primer (green), T7 terminator reverse primer (blue), both T7 forward and reverse primers (grey). Control primers were used (purple) with no peptides.
Figures 11A, 11B:
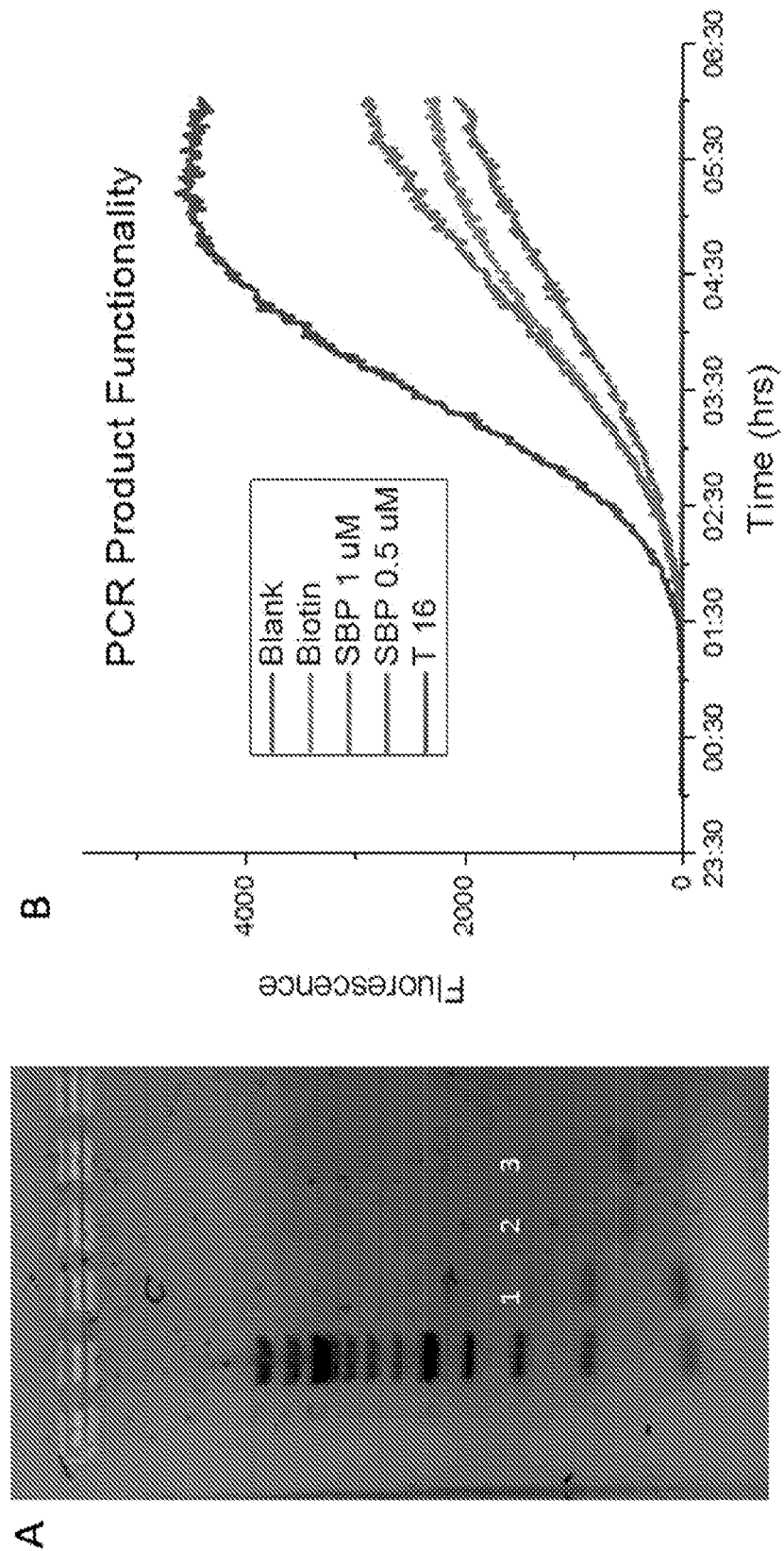
FIGS. 11A-11B demonstrate PCR product characterization. A. Shows 2% agarose gel of 1, PCR product from Biotin-T7 term. reverse primer. 2, product from 0.5 µM SBP-T7 term. reverse primer. 3, Product from 1 µM SBP-T7 term. reverse primer. B. Shows product functionality is maintained in cell-free reactions with a toehold switch. Triggers transcribed from templates have streptavidin binding peptide (SBP) and biotin modifications can be successfully transcribed and used to activate the cognate toehold switch, which expresses GFP. Output from a negative control shows no fluorescence output from toehold switch.

Peptide was conjugated to the 5' end of T7 promoter forward and T7 terminator reverse primers using copper-free click chemistry. These two primers are designed to bind to universal sequences that flank nearly all the trigger expression cassettes in the riboregulators that our group has developed. These cassettes employ the T7 promoter to direct binding of T7 RNA polymerase for transcription and have a T7 terminator to halt transcription from the plasmid. Different primer concentrations were tested for reaction optimization and we evaluated multiple combinations of peptide-conjugated and unmodified primers. The data show only a slight increase in product concentration as initial primer concentration was increased compared to the control (FIG. 10). Peptide attachment was detected using a fluorescein (FITC) molecule linked to the peptide. The PCR product was analyzed using gel electrophoresis for size and charge and concentrations were obtained measuring the absorbance at 260 nm for DNA and 495 nm for FITC. Results showed the T7 promoter primer conjugate was not as effective in initiating amplification of the trigger plasmid in PCR based off product yield (FIG. 10). We attribute the weaker performance of this primer to its low melting temperature, which we plan to increase in future experiments. Because of this, only the T7 terminator reverse primer conjugate was used for later experiments. Although the peptide-DNA primers did not show the same substantial increases in yield that were observed for the control unmodified primer set, the typical primer concentration used in PCR reactions is 0.5 µM. For the 0.5 µM primer concentrations, the performance of the T7 terminator reverse primer conjugate provided very similar yields to the control primers. Several different peptides-primer conjugates were also tested along with biotin conjugated T7 terminator reverse primer purchased from IDT (FIG. 11A).

Double-stranded PCR products from biotin- and SBP-attached primers were also tested for functionality of toehold switch activation using a cell-free system. Results showed toehold activation, indicating not only PCR dsDNA product functionality was maintained but that the product could be transcribed with the SBP peptide attached in the cell-free system (FIG. 11B). Taken together, these results demonstrate that peptides can be readily conjugated to dsDNA using a simple amplification procedure and that the resulting product does not interfere with recognition by an RNA polymerase for transcription of a trigger RNA. These capabilities will enable the cost of the assay to be reduced and lower the detection limits of the resulting diagnostic devices.

Figure 12:
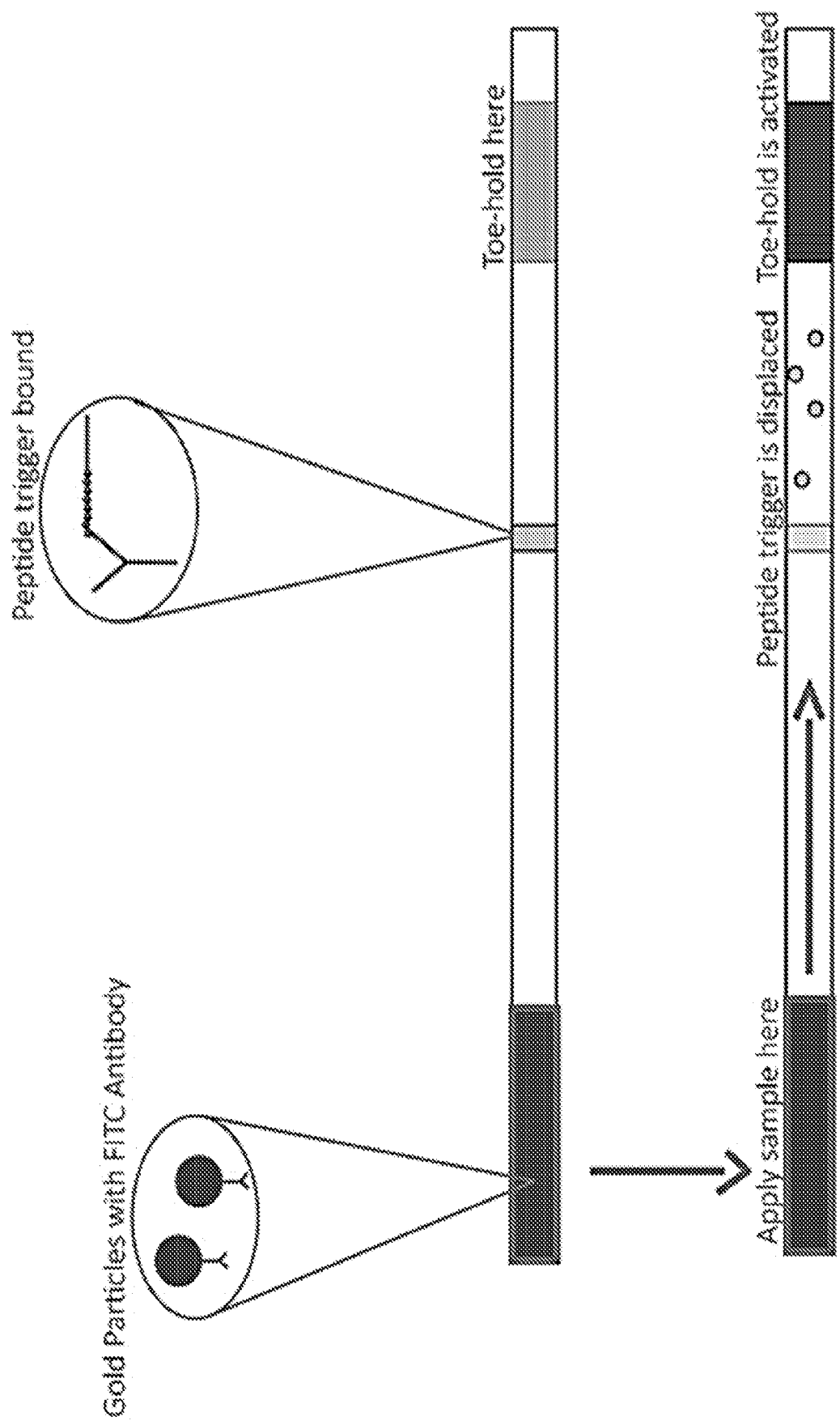
FIG. 12 illustrates an exemplary lateral flow assay design. Sample is added to the red region. Capillary forces flow sample through the assay. Sample then interacts with DNA-peptide trigger and displaces it from target antibody/protein (green). The trigger then continues to flow down to toehold region (pink). Toehold is activated and reporter protein is expressed leading to a visible color change.

3) Implementation of Peptide Displacement Reactions in Paper Test Strips:

Lateral flow assays based on paper test strips were studied as a means to test the ability of a peptide-DNA conjugate to be displaced upon detection of a target analyte. For a proof-of-concept assay, we aimed to bind the signal peptide-DNA conjugate to a test band line in the strip (FIG. 12). When the sample is supplied, the analyte will move along the strip through capillary forces and displace the peptide-DNA conjugate. The released signal molecule will then migrate to a cell-free reaction area where the peptide-DNA leads to activation of the cognate riboregulator to produce a visible readout. Successful implementation of this device would confirm the functionality of the main components of the proposed protein detection system: peptide-DNA displacement via analyte binding, movement of the peptide-DNA signal into a cell-free reaction zone, and readout of the signal presence via a riboregulator-based cell-free assay.

We first studied peptide displacement using the paper test strips. For these experiments, we employed a streptavidin-binding peptide (SBP) to bind to a commercial lateral flow test strip (Milenia HybriDetect, TwistDx Ltd.). These lateral flow strips have a test band containing streptavidin and a sample receiving area containing gold nanoparticles decorated with anti-FITC antibodies. A control band is positioned downstream of the test band and contains a secondary antibody for binding the conserved region of the anti-FITC antibody.

Figure 13A:
FIGS. 13A-13B demonstrate peptide binding to a lateral flow assay. Panel A shows the binding of peptide, visible with first purple band formation. Panel B shows displacement of band formation after addition of biotin.
Figure 13B:

To enable detection using anti-FITC antibodies, the SBP peptide was further conjugated to FITC to produce SBP-FITC. SBP-FITC conjugates were first bound to the streptavidin test band by applying them in an aqueous solution to the sample receiving area (FIGS. 13A-13B, left side of strips). Bound SBP-FITC could be readily identified by the appearance of a purple band at the streptavidin line caused by the concentration of gold nanoparticles decorated with anti-FITC antibodies. To demonstrate peptide displacement, we then supplied the analyte biotin to the sample application region. The biotin, which has extremely high affinity for streptavidin, caused the purple test band to disappear rapidly (FIG. 13B). Dissolution of the band occurred primarily because the biotin displaced the SBP-FITC from the streptavidin, enabling the bound gold nanoparticles to move with the fluid toward right side of the strips.

Figure 14:
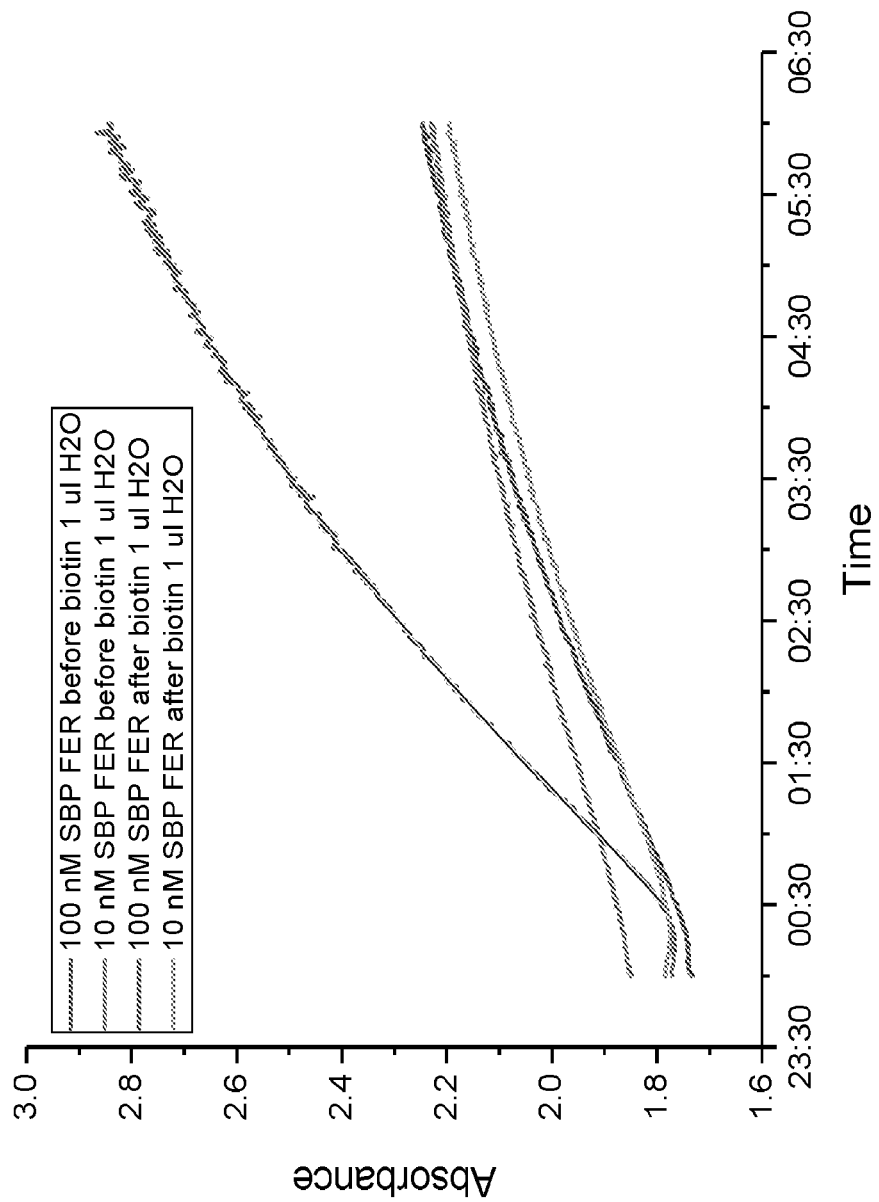
FIG. 14 demonstrates detection of peptide displacement using a combined DNA-peptide cell-free toehold switch test strip assay. Absorbance of a cell-free paper-based reaction was observed over time using a toehold switch regulating lacZ. After displacement by a biotin solution, the SBP-FER1_T16 prepared on the test strip at 100 nM concentration was able to successfully activate the cell-free reaction.

We then implemented our proof-of-concept test by taking a conjugate consisting of SBP bound to the FER1_T16 DNA trigger sequence (SBP-FER1_T16). The conjugate was first applied to the sample area and allowed to bind to the streptavidin test band. Concentrations of 10 nM and 100 nM of SBP-FER1_T16 were evaluated to determine the optimal level for toehold switch activation. Following binding to streptavidin, excess SBP-FER1_T16 conjugates were then rinsed away by applying extra water to the sample receiving area. After this step, a biotin solution was applied as a sample while comparison experiments were conducted by applying water alone. After flow through of the sample had occurred, paper disks containing the cell-free systems and toehold switch FER1_H16 regulating lacZ were then contacted to the strip downstream of the control line and rehydrated to activate the cell-free reaction. We observed the resulting color-change reactions in a plate reader to assess activation of the toehold switch by any displaced SBP-FER1_T16 signal molecules (FIG. 14). As expected, we did not see activation of the toehold switch when a water solution was added to the test strip, since the signal molecules were not displaced. In contrast, the strip seeded with 100 nM of SBP-FER1_T16 displayed a significant color change after addition of biotin, indicating successful displacement of the DNA-peptide conjugate by the cognate ligand. We further found that 10 nM of SBP-FER1_T16 was unable to activate the toehold switch, likely because its concentration was too low for the sensitivity of the FER1_H16 toehold switch. We expect that transcription of a dsDNA peptide-DNA trigger or an isothermal amplification step will substantially improve the sensitivity of the assay, enabling lower concentrations of peptide-DNA to be used for preparing the assay strips.

The above research demonstrates the working components of a paper-based diagnostic that combines the ease of use and sensitivity of nucleic acid tests with the profound importance of other biomolecules such as proteins, antibodies, carbohydrates, and lipids in reporting human health. Upon completion, the working components will result in a synthetic gene network with the ability to respond to multiple nucleic acid and non-nucleic acid signals. In the presence of a target protein, a DNA-peptide conjugate is displaced from a target antibody. The DNA-peptide conjugate can then interact with a toehold switch, activating gene expression of a measurable protein. To expand on this project, we look to incorporate the use of peptide arrays, making it a cost-effective diagnostic to profile a wide range of diseases where a single biomarker is insufficient for conclusively identifying an illness. Applying this network to an array of peptides will provide a novel way to directly measure the products of the immune system through protein-to-nucleic signal transduction, creating a new class of diagnostics. This concept will result in a universal diagnostic that has durability and accessibility required for real world applications in global health.

Methods:

Toehold selection and construction: The trigger and toehold plasmid inserts were constructed using PCR. This was done through the combination of two linear constructs, containing the origin of replication site and antibiotic resistance gene, and the riboregulator or trigger sequence. Both plasmids contain T7 promoter and T7 terminator regions.

The toehold plasmid also contains the coding sequence for either GFP or LacZ to monitor toehold activation.

Synthesis of DNA-Peptide Conjugate: Peptides were synthesized using solid phase peptide synthesis or purchased from Watson biotech with a non-canonical azidolysine at the N-terminus. Peptides synthesized from solid phase peptide synthesis were purified using high pressure liquid chromatography (HPLC) and characterized using matrix-assisted laser desorption/ionization mass spectrometry and gel electrophoresis. Peptides purchased from Watsonbio were >90% HPLC purity grade and no further purification was needed.

While the preferred embodiments of the present invention have been illustrated in detail, it should be apparent that modifications and adaptations to those embodiments may occur to one skilled in the art without departing from the scope of the present invention as set forth in the following claims.

We claim:

1. A diagnostic device for detecting a target analyte in a sample, the device having a layered architecture and comprising, in order, a sample receiving layer, an analyte detection layer, a nucleic acid amplification layer, a microfluidic layer, one or more biomolecular computing layers, and an output layer,
   wherein the layered architecture allows for transverse liquid flow predominantly perpendicular to the length and width of each layer such that the sample is drawn from the sample receiving layer to one or more subsequent layers and the layers of the diagnostic device are separated by one or more transient layers positioned between the sample receiving layer and the analyte detection layer, the analyte detection layer and the nucleic acid amplification layer, or the nucleic acid amplification layer and the microfluidic layer that dissolve in a prescribed amount of time when contacted to the sample to control transverse flow through the device,
   wherein the analyte detection layer comprises a plurality of antibodies or epitopes fixed to paper and at least one of the plurality of antibodies or epitopes have a peptide-DNA conjugate bound thereto, wherein the plurality of antibodies or epitopes have specificity for the target analyte, and wherein binding of the target analyte to the at least one of the plurality of antibodies or epitopes having the peptide-DNA conjugate bound thereto displaces the bound peptide-DNA conjugate,
   wherein the amplification layer amplifies a nucleic acid in the sample, the peptide-DNA conjugate, or a combination thereof,
   wherein the microfluidic layer is patterned to controllably distribute the amplified nucleic acid in the sample, the amplified peptide-DNA conjugate, or the combination thereof laterally across the length and/or width of the microfluidic later,
   wherein the one or more biomolecular computing layers employ nucleic acid interactions to perform a logic operation to generate a computational output,
   wherein the output layer comprises a nucleic acid-based sensor reaction panel,
   and wherein each of the sample receiving layer, the analyte detection layer, the nucleic acid amplification layer, the microfluidic layer, the one or more biomolecular computing layers, and the output layer are paper-based.

2. The device of claim 1, wherein the target analyte is a protein, carbohydrate, or lipid.

3. The device of claim 1, wherein the sample receiving layer comprises a separation membrane.

4. The device of claim 1, wherein the sample is a biological sample.

5. The device of claim 4, wherein the biological sample is a blood, serum, plasma, urine, or saliva sample.

6. The device of claim 1, wherein the nucleic acid-based sensor reaction panel comprises a plurality of nucleic acid-based sensors.

7. The device of claim 6, wherein the plurality comprises nucleic acid-based sensors selected from the group consisting of a riboregulator and an aptasensor.

8. The device of claim 1, wherein the one or more transient layers comprise a dried sucrose solution.

9. The device of claim 1, wherein the device comprises transient layers positioned between the sample receiving layer and the analyte detection layer, the analyte detection layer and the nucleic acid amplification layer, and the nucleic acid amplification layer and the microfluidic layer that dissolve in a prescribed amount of time when contacted to the sample to control transverse flow through the device.

10. The device of claim 9, wherein the transient layers comprise a dried sucrose solution.

* * * * *